(12) United States Patent  
Garibotto et al.

(10) Patent No.: US 7,316,655 B2
(45) Date of Patent: Jan. 8, 2008

(54) SYSTEMS AND METHODS FOR DIRECTING AND SNARING GUIDEWIRES

(75) Inventors: John Garibotto, Palo Alto, CA (US); Steven W. Kim, San Jose, CA (US); Jason Whitt, San Francisco, CA (US); J. Christopher Flaherty, Los Altos, CA (US); Joshua Makower, Los Altos, CA (US); Motoya Hayase, Palo Alto, CA (US); John Chang, Santa Clara, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 891 days.

(21) Appl. No.: 10/136,929

(22) Filed: Apr. 30, 2002

(65) Prior Publication Data

US 2002/0123698 A1 Sep. 5, 2002

Related U.S. Application Data

(60) Division of application No. 09/179,737, filed on Oct. 27, 1998, now Pat. No. 6,379,319, which is a continuation-in-part of application No. 08/970,694, filed on Nov. 14, 1997, now Pat. No. 6,432,127, which is a continuation-in-part of application No. 08/730,327, filed on Oct. 11, 1996, now Pat. No. 6,190,353.

(51) Int. Cl.
*A61B 5/00* (2006.01)
*A61M 25/00* (2006.01)

(52) U.S. Cl. ..................................... 600/585

(58) Field of Classification Search ............... 600/585, 600/107, 434; 604/506, 104, 164.13, 264, 604/523, 272, 102.02, 9.5, 164.08, 535; 623/1.11, 623/1.35; 606/195, 194

See application file for complete search history.

(56) References Cited

U.S. PATENT DOCUMENTS 3,516,408 A 6/1970 Montanti (Continued)

FOREIGN PATENT DOCUMENTS

EP 200668 4/1986

(Continued)

OTHER PUBLICATIONS

Steven L. Schwartz, M.D., et al., "Real-Time Intracardiac Two-Dimensional Echocardiography: An Experimental Study in In Vivo Feasibility, Imaging Planes, and Echocardiographic Anatomy", Echocardiography: A Jrnl. of CV Ultrasound & Allied Tech. vol. 7(4): 443-455, (1990).
Michael Von Ludinghausen, et al., "Atrial Veins of the Human Heart", Clinical Anatomy 8: 169-189 (1995).

*Primary Examiner*—Max F. Hindenburg
*Assistant Examiner*—Brian Szmal

(57) ABSTRACT

Devices and methods for achieving directed placement of guidewires or other flexible rails over which other catheters or other devices may be introduced to a targeted location. A guidewire directing device includes a lumen extending between a proximal end and a distal peripheral opening for directing a guidewire laterally from the device, and may have a deflecting member with a predetermined deflection angle in the lumen adjacent the peripheral opening. A snaring device is also provided that includes one or more lumens through which a snare or other grasping member is directed for releasably capturing or coupling to a guidewire. The snaring and target guidewire devices may include cooperating end effectors for releasably coupling or securing the devices together. The devices may be used for directing, snaring and/or manipulating one or more guidewires between two blood vessels connected by an interstitial channel, for example, to "floss" a guidewire through the coronary arterial and venous systems between two percutaneous entry sites and/or to bypass a lesion in a vessel using proximal and distal interstitial channels communicating with an adjacent vessel.

22 Claims, 26 Drawing Sheets

U.S. PATENT DOCUMENTS

| | | | |
|---|---|---|---|
| 4,452,236 A * | 6/1984 | Utsugi | 600/107 |
| 4,552,554 A * | 11/1985 | Gould et al. | 604/506 |
| 4,739,768 A | 4/1988 | Engelson | 128/658 |
| 4,769,005 A | 9/1988 | Ginsburg et al. | 604/53 |
| 4,774,949 A | 10/1988 | Fogarty | 128/348.1 |
| 4,861,336 A | 8/1989 | Helzel | 604/95 |
| 4,927,426 A | 5/1990 | Dretler | 606/128 |
| 5,019,090 A | 5/1991 | Pinchuk | 606/194 |
| 5,047,039 A | 9/1991 | Avant et al. | |
| 5,054,492 A | 10/1991 | Scribner et al. | 128/662.06 |
| 5,059,177 A * | 10/1991 | Towne et al. | 604/102.02 |
| 5,108,406 A | 4/1992 | Lee | 606/106 |
| 5,171,233 A | 12/1992 | Amplatz et al. | 604/281 |
| 5,180,367 A | 1/1993 | Kontos et al. | |
| 5,220,924 A | 6/1993 | Frazin | 128/662.06 |
| 5,282,810 A | 2/1994 | Allen et al. | |
| 5,287,861 A | 2/1994 | Wilk | |
| 5,312,341 A | 5/1994 | Turi | |
| 5,334,185 A | 8/1994 | Giesy et al. | |
| 5,342,371 A | 8/1994 | Welter et al. | 606/113 |
| 5,354,279 A | 10/1994 | Hofling | 604/164 |
| 5,366,490 A | 11/1994 | Edwards et al. | 607/99 |
| 5,409,019 A | 4/1995 | Wilk | |
| 5,429,144 A | 7/1995 | Wilk | |
| 5,443,497 A | 8/1995 | Venbrux | |
| 5,452,733 A | 9/1995 | Sterman et al. | |
| 5,464,395 A | 11/1995 | Faxon et al. | 604/96 |
| 5,499,630 A | 3/1996 | Hiki et al. | 128/662.05 |
| 5,522,819 A | 6/1996 | Graves et al. | 606/113 |
| 5,540,236 A | 7/1996 | Ginn | 128/772 |
| 5,556,380 A | 9/1996 | Ridinger et al. | 604/52 |
| 5,599,300 A | 2/1997 | Weaver et al. | 604/54 |
| 5,624,430 A | 4/1997 | Eton et al. | 606/1 |
| 5,643,281 A | 7/1997 | Suhocki et al. | 606/113 |
| 5,662,671 A | 9/1997 | Barbut et al. | 606/170 |
| 5,697,936 A | 12/1997 | Shipko et al. | 606/108 |
| 5,713,363 A | 2/1998 | Seward et al. | 128/662.06 |
| 5,749,370 A | 5/1998 | Brooks et al. | 128/772 |
| 5,752,961 A | 5/1998 | Hill | 606/113 |
| 5,769,868 A | 6/1998 | Yock | 606/194 |
| 5,776,079 A | 7/1998 | Cope et al. | 600/585 |
| 5,779,669 A | 7/1998 | Haissaguerre et al. | 604/95 |
| 5,779,722 A | 7/1998 | Shturman et al. | 606/159 |
| 5,824,055 A * | 10/1998 | Spiridigliozzi et al. | 623/1.11 |
| 5,840,066 A * | 11/1998 | Matsuda et al. | 604/102.02 |
| 5,947,925 A * | 9/1999 | Ashiya et al. | 604/164.08 |
| 5,972,017 A | 10/1999 | Berg et al. | |
| 5,976,178 A | 11/1999 | Goldsteen et al. | |
| 6,001,124 A | 12/1999 | Bachinski | |
| 6,013,190 A | 1/2000 | Berg et al. | |
| 6,036,702 A | 3/2000 | Bachinski et al. | |
| 6,068,654 A | 5/2000 | Berg et al. | |
| 6,120,432 A | 9/2000 | Sullivan et al. | |
| 6,231,563 B1 | 5/2001 | White et al. | |
| 6,511,458 B2 * | 1/2003 | Milo et al. | 604/164.13 |

FOREIGN PATENT DOCUMENTS

| | | |
|---|---|---|
| WO | 9701988 | 1/1997 |
| WO | 9733522 | 9/1997 |
| WO | 9738630 | 10/1997 |
| WO | 9819608 | 5/1998 |
| WO | 9819618 | 5/1998 |
| WO | 9819630 | 5/1998 |
| WO | 9819634 | 5/1998 |
| WO | 9819636 | 5/1998 |
| WO | 9819732 | 5/1998 |
| WO | 9838939 | 9/1998 |
| WO | 9838941 | 9/1998 |
| WO | 9838942 | 9/1998 |

* cited by examiner

SYSTEMS AND METHODS FOR DIRECTING AND SNARING GUIDEWIRES

This application is a divisional of application Ser. No. 09/179,737, filed Oct. 27, 1998, issuing as U.S. Pat. No. 6,379,319, which is a continuation-in-part of application Ser. No. 08/970,694, filed Nov. 14, 1997, now U.S. Pat. No. 6,432,127 which is a continuation-in-part of application Ser. No. 08/730,327, filed Oct. 11, 1996, now U.S. Pat. No. 6,190,353 the disclosures of which are expressly incorporated herein by reference.

FIELD OF THE INVENTION

The present invention relates to devices and methods for manipulating and directing guidewires and other "rails," e.g. catheters, within the human vasculature, over or through which other devices are then introduced into the vasculature to perform a medical procedure.

BACKGROUND

In the field of vascular intervention, and more specifically in the field of interventional cardiology, devices known as guidewires are often used to facilitate access to a patient's vascular system, placement of various devices and/or performance of certain procedures. A guidewire is maneuvered into place to act as a guide for positioning the placement of subsequent devices "over the wire." The guidewire, typically ranging from 0.010" to 0.038" inch diameter, as compared to an interventional catheter which may range from 0.040" to 0.25" inch diameter, is extremely flexible and tracks easily into a patient's vessels, allowing the physician to obtain an initial position, and many times to find the optimal position, in the vasculature prior to tracking a larger interventional catheter over the wire to perform an intervention. In addition, a guidewire may maintain access to a certain site in the vasculature should it be necessary for the physician to use multiple devices to perform an intervention at the site, or to perform multiple interventions at different sites in the vasculature.

Due to their flexibility, guidewire access minimizes trauma to the vessel being treated and assists in directing or guiding other devices through the curvature and tortuosity of the vascular system. Unwanted trauma may include "skiving" of the vessel, wherein a less flexible device may scrape the vessel wall at an undesired angle, and unintended perforation, wherein a device may be pushed through the vessel wall in an uncontrolled manner, leading to excessive bleeding (tamponade) and/or other severe patient complications.

Guidewires act as a rail over which other less flexible and larger diameter devices may be delivered safely, thereby reducing the risk of unwanted vessel trauma. In current medical practice, guidewire access and performance of procedures "over the wire" are the preferred mode of vascular device delivery. As such, it is critical to the clinical acceptance of new devices and therapies for them to be compatible with this technique, and to be delivered over the wire.

In light of the development of certain clinical procedures, there is a need for devices and methods that more specifically direct, place and maintain a guidewire or other rail at one or more selected locations in the vasculature.

SUMMARY OF THE INVENTION

The present invention is directed to various devices and methods for achieving directed placement of guidewires or other flexible rails over which other catheters or other devices may be introduced to a targeted location. For example, the devices and methods of the present invention may be incorporated into novel clinical procedures, such as those disclosed in U.S. patent application Ser. No. 08/730,327, filed Oct. 11, 1996, Ser. No. 08/730,496, filed Oct. 11, 1996, and Ser. No. 08/970,694, filed Nov. 14, 1997, the disclosures of which are expressly incorporated herein by reference.

Several of these procedures are performed in an "extravascular" location (e.g., from vessel to vessel, from vessel to another structure, or from vessel to another location or space within the body), necessitating the positioning of guidewires outside the normal "intraluminal" location within the vessel itself. It may also be necessary to "orient" the entrance and exit of guidewires between vessels to better control the angle of placement of subsequently placed devices.

Further, in the case where multiple devices are tracked over the wire subsequent to initial placement, it may be necessary to stabilize the wire within the vessel or other location to minimize potential vessel trauma due to multiple manipulations of subsequently placed devices. Also it may be necessary to minimize potential loss of placement of the guidewire should it become displaced in response to forces exerted on it by catheters as they are advanced or removed from the vessel.

In one aspect of the present invention, devices are provided for directing a guidewire, catheter or other rail substantially laterally with respect to a body passage within which the device is introduced. In a first preferred embodiment, the device includes an elongate member having proximal and distal ends, having a distal portion adapted for insertion within a body passage, and defining a longitudinal axis and an outer peripheral surface. A lumen extends between the proximal end and a peripheral opening in the distal portion, and a deflecting member is provided therein adjacent to the peripheral opening for directing a guidewire device substantially laterally with respect to the longitudinal axis.

Preferably, the deflecting member has a predetermined acute deflection angle for directing the guidewire device substantially distally and laterally. Alternatively, the deflecting member may have a predetermined oblique deflection angle for directing the guidewire device substantially proximally and laterally. In a preferred form, the guidewire device is a needle assembly having a guidewire lumen extending therethrough, although alternatively, the guidewire device may simply be a guidewire alone, which may be deflected substantially laterally when it contacts the deflection member and is advanced through the peripheral opening. In addition, the device may include an imaging and/or orientation element on the distal portion, such as a radiopaque marker, having a predetermined relationship with the peripheral opening.

In a second preferred embodiment, a catheter is provided for directing a guidewire substantially laterally with respect to a body passage within which the catheter is introduced. The catheter is an elongate member having proximal and distal ends, having a distal portion adapted for insertion within a body passage, and defining a longitudinal axis and an outer peripheral surface. A first lumen extends between the proximal end and a first axial opening in the distal end, and a second lumen extends between the proximal end and a second lateral opening in the distal portion proximate the distal end.

Preferably, the second lateral opening is located on the peripheral surface of the elongate member, and the second lumen includes a deflection ramp therein adjacent to the second lateral opening. In addition, the distal portion may include an angled step tapering to a distal tip, the second lateral opening being located on the angled step.

In another aspect of the present invention, devices are provided for releasably snaring a guidewire or other rail, e.g., to facilitate placement or manipulation of the guidewire. In a preferred embodiment, the snaring device includes an elongate member having proximal and distal portions, and having first and second lumens extending between the proximal and distal portions. The first lumen has a first distal opening proximate to a second distal opening of the second lumen on the distal portion.

A snaring member including a loop on its distal end is slidably received in the first lumen, the loop extending distally from the first distal opening and surrounding the distal portion of the elongate member such that the snaring member may be directed proximally and distally, the loop thereby substantially engaging and disengaging, respectively, an outer surface of the distal portion of the elongate member.

The loop may be biased to assume an enlarged substantially circular configuration, the substantially circular configuration preferably defining a predetermined diameter corresponding to a diameter of a lumen of a blood vessel. The corresponding distal portion of the elongate member has a diameter substantially smaller than the predetermined diameter. Preferably, the distal portion includes an angled step tapering to a distal tip, the first distal opening being located on the angled step, and the second distal opening being located on the distal tip.

In an alternative form, the snaring device includes an elongate member having proximal and distal ends, having a distal portion adapted for insertion within a body passage, and defining a longitudinal axis and an outer peripheral surface. A lumen extends between the proximal end and a peripheral opening in the distal portion. A snaring member is deployable substantially laterally from the peripheral opening, and includes a snare on its distal end, which may be retractable within a lumen in the snaring member, or otherwise adapted for releasably securing a guidewire device to the snaring member.

In another preferred embodiment, a system including cooperating end effectors is provided for placing and/or directing guidewire devices with respect to adjacent body passages, e.g., through an interstitial channel between two adjacent blood vessels. The system includes an elongate guidewire device having a substantially flexible distal portion having a size adapted for insertion within a blood vessel, and a directing member having a proximal end and a distal end having a size adapted for insertion within a blood vessel. The directing member defines a longitudinal axis, and has a portion that is directable substantially laterally with respect to the longitudinal axis, for example by providing a distal portion of the directing member having a precurved shape.

Cooperating end effectors are provided on the distal portion of the guidewire device and the distal end of the directing member for detachably securing the distal portion of the guidewire device and the distal end of the directing member together. In one form, the end effectors may include a magnet on the guidewire device and/or the directing member. Alternatively, the directing member may include a mechanical grasping mechanism, such as cooperating jaws or an expandable basket structure.

In another form, the end effectors may include a tip with a recess therein on one of the guidewire device or the directing member, and a loop and pin on the other of the guidewire device or the directing member. The loop defines an aperture adapted to receive the tip therethrough, the pin being deployable within the aperture to detachably engage the recess.

In still another form, the directing member may be a catheter device having at least one lumen extending between the proximal and distal ends thereof. An end effector may be deployable from the distal end of the directing member through the at least one lumen. The end effector on the guidewire device may be an enlarged distal tip to facilitate capture by the catheter device. For example, the end effector on the catheter device may be a snare including a loop adapted to receive the enlarged distal tip on the guidewire device therethrough.

The snare may be deployed through a single lumen in the catheter device, or alternatively, the catheter device may include first and second lumens. The snare may then include a looped wire having first and second ends which extend proximally through the first and second lumens, respectively, to define an enclosed loop extending beyond the distal end. Alternatively, the snare may be a basket assembly expandable between contracted and enlarged conditions.

The devices and systems according to the present invention may be used in a variety of procedures for directing, snaring and/or manipulating one or more guidewires, catheters or other rails between two locations within one or more body passages. For example, in accordance with the present invention, a method is provided for directing an elongate guidewire device between two body passages connected by an interstitial channel, preferably between two blood vessels within the coronary system. A guidewire device may be advanced along a first vessel to a location adjacent to an interstitial channel communicating with a second vessel. A snaring member may be advanced along the second vessel and through the interstitial channel into the first vessel.

A distal end of the guidewire device may be snared, captured or otherwise releasably coupled to the snaring member, and the snaring member may be withdrawn through the interstitial channel back into the second vessel, thereby pulling the distal end of the guidewire device into the second vessel. The distal end of the guidewire device may then be released from the snaring member within the second vessel. Before releasing the distal end of the guidewire device, the snaring member may also be directed along the second vessel to a predetermined location.

In another method according to the present invention, a guidewire may be placed in a predetermined orientation between two blood vessels within a patient's body, preferably between a vein and an artery, more preferably between a coronary vein and a coronary artery. A distal end of a first guidewire may be advanced distally from a first percutaneous entry site into a first vessel adjacent a proximal channel between the first vessel and a second vessel. A snaring member may be advanced from a second percutaneous entry site distally into the second vessel adjacent the proximal channel.

The distal end of the first guidewire or the snaring member may be advanced through the proximal channel, and the distal end of the first guidewire may be snared with, or otherwise coupled to, the snaring member. The snaring member may be withdrawn proximally from the second vessel and out the second entry site, thereby "flossing" the first guidewire through the first and second vessels between the first and second entry sites.

A catheter may be advanced from the second entry site over the flossed first guidewire into the second vessel adjacent the proximal channel, and a snaring member advanced from the first entry site into the first vessel. A second guidewire may be deployed from the catheter, and either the catheter, the second guidewire or the snaring member advanced through the proximal channel. A distal end of the second guidewire may be snared with the snaring member, and then the snaring member may be directed proximally or distally along the first vessel to a selected location. The distal end of the second guidewire may be released from the snaring member at the selected location.

Preferably, the selected location is a distal location in the second vessel, and the snaring member is advanced through a distal channel from the first vessel into the second vessel to advance the second guidewire into the distal location in the second vessel. The snaring member may be advanced through the distal channel over a fourth guidewire previously placed from the first entry site through the first vessel and the distal channel into the distal location in the second vessel. Thus, the second guidewire may facilitate a procedure to bypass a lesion in the second vessel at a location between the proximal and distal channels.

The devices and methods of the present invention may facilitate directed placement of guidewires or other flexible rails within a patient's body over which other catheters or interventional devices may be introduced. One or more guidewire directing catheters and/or one or more snaring devices for grasping or capturing guidewires may be used in a variety of procedures to achieve desired control and placement of the guidewires. Thus, unlike conventional snaring devices, which substantially permanently snare guidewires for removal from a patient's body, the devices and methods of the present invention facilitate "reversibility," i.e., the ability to selectively snare, direct and release rails within a patient's body.

Other objects and features of the present invention will become apparent from consideration of the following description taken in conjunction with the accompanying drawings.

DETAILED DESCRIPTION OF THE PREFERRED EMBODIMENTS

Figure 1A:
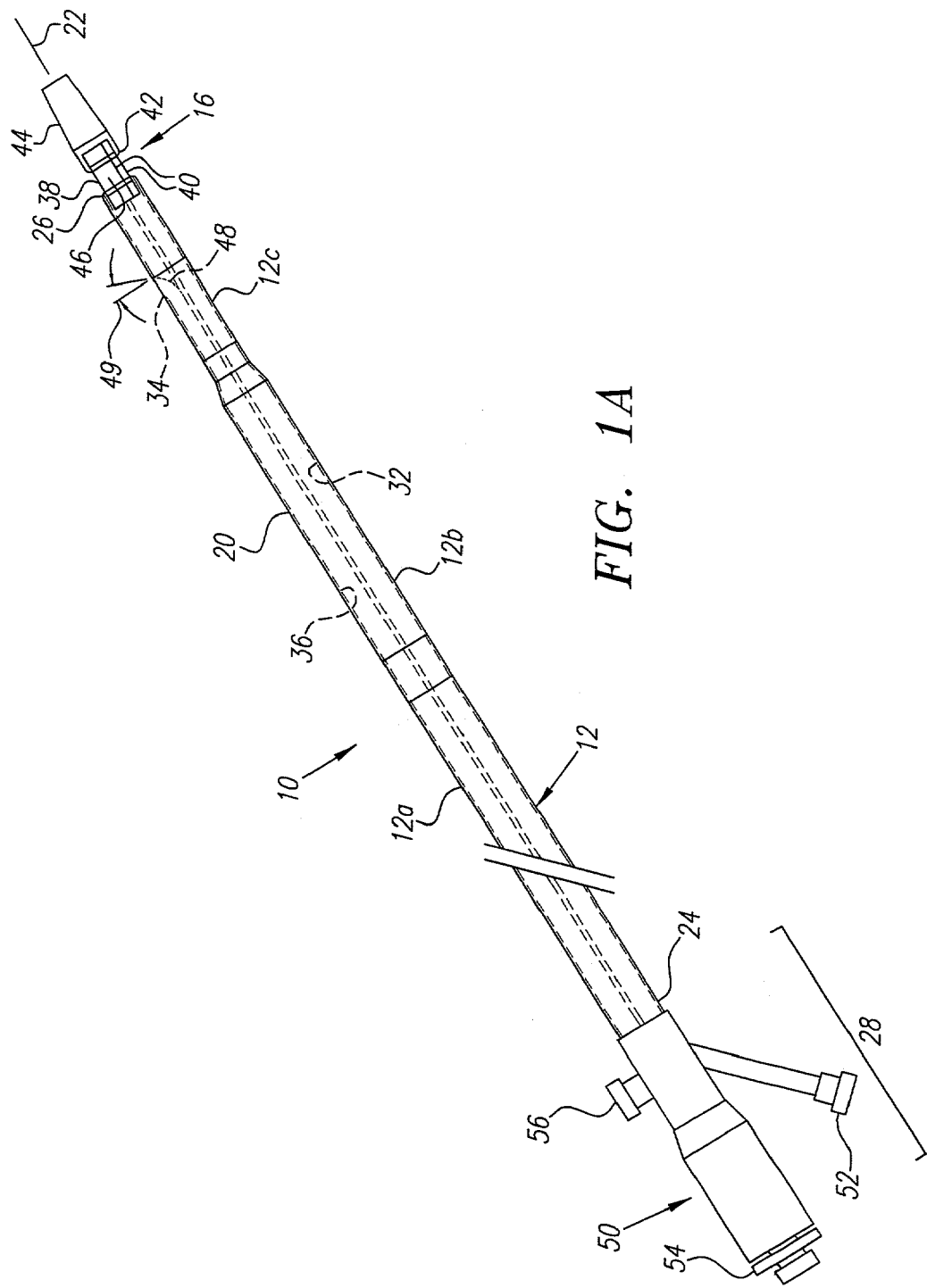
FIG. 1A is a cross-sectional view of a catheter device for directing a guidewire, in accordance with one aspect of the present invention.
Figure 1B:
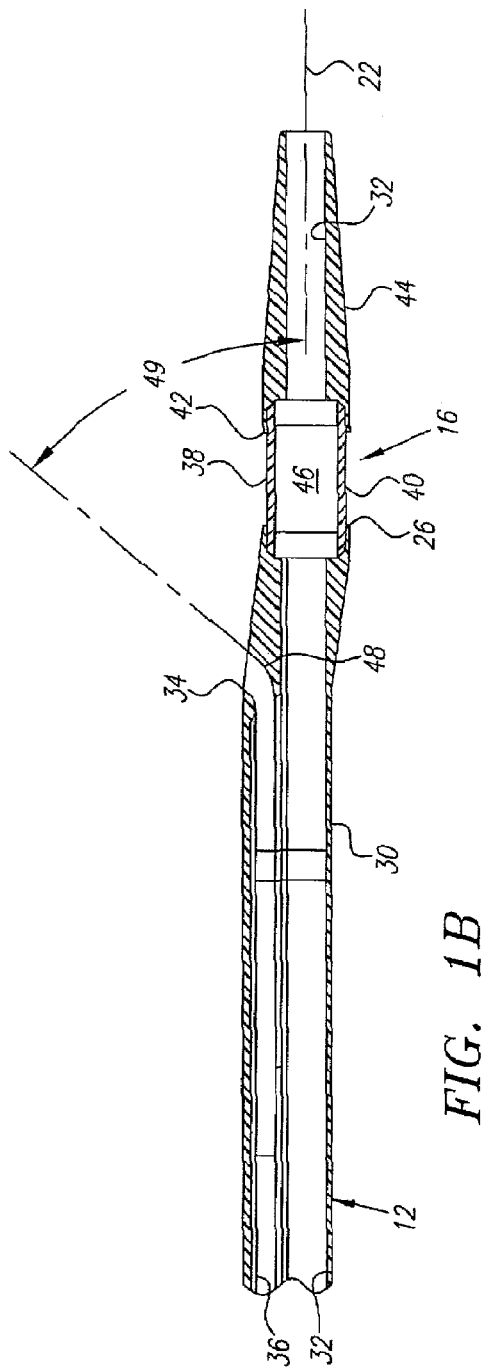
FIG. 1B is a cross-sectional view of a distal portion of the catheter device of FIG. 1A.

In a first aspect of the present invention, systems and methods are provided for directing a guidewire or other rail in a predetermined direction and/or angle with respect to a body passage, e.g., within a single blood vessel or preferably through a channel between adjacent vessels, within which the guidewire is deployed. Turning to the drawings, FIGS. 1A and 1B show a first preferred embodiment of a catheter device 10 for directing a guidewire (not shown) in ID accordance with the present invention. The catheter device 10 includes an elongate catheter 12 having substantially flexible and/or semi-rigid sections, and defining a circumference or periphery 20 and a longitudinal axis 22 between its proximal and distal ends 24, 26. The catheter 12 includes a proximal portion 28 having a handle 50 and a distal portion 30 having a size and shape for facilitating insertion into a blood vessel.

Figure 1C:
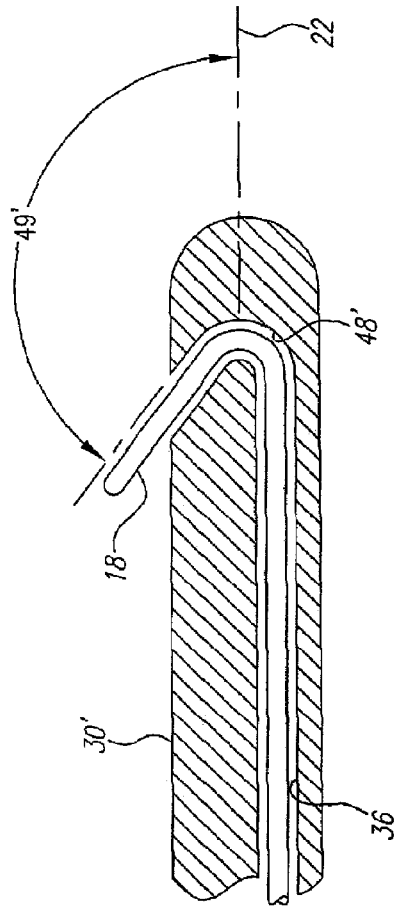
FIG. 1C is a cross-sectional view of an alternate embodiment of the distal portion of the catheter device of FIG. 1A, showing a guidewire being deployed therefrom.

A guidewire lumen 36 extends from an entry port 54 in the handle 50 to a peripheral opening 34 in the distal portion 30 for receiving a guidewire or other rail (not shown) therethrough. A needle lumen flush port 56 may be provided in the handle 50 in communication with the guidewire lumen 36 for introducing fluid to flush the guidewire lumen 36. The guidewire lumen 36 includes a deflecting element or ramp 48 therein adjacent to the peripheral 20 opening 34 having a substantially acute deflection angle 49. The deflecting ramp 48, with the deflection angle 49 preferably ranging from about 30-90° and more preferably about 30-60°, allows a guidewire deployed from the guidewire lumen 36 to be directed substantially laterally and distally with respect to the longitudinal axis 22, preferably at an angle ranging from about 30-90° and more preferably about 30-60°. Alternatively, as shown in FIG. 1C, the deflecting ramp 48' may have a substantially oblique deflection angle 49', preferably ranging from about 90-150° and more preferably about 120-150°, to direct a guidewire 18 substantially laterally and proximally, i.e., laterally with respect to the longitudinal axis 22 but directed generally towards the proximal end 24 of the catheter device 10.

The catheter 12 may include an extruded dual lumen catheter body encapsulated within an outer jacket (not shown) and/or may have a proximal portion that is substantially more rigid than a distal portion. For example, the catheter 12 may include a proximal portion 12a, an intermediate portion 12b, and a distal portion 12c (see FIG. 1A), each having a dual lumen catheter segment and an outer jacket segment. The rigidity or Durometer of the dual lumen catheter and outer jacket segments of the proximal portion 12a is preferably about 63 and about 70, respectively, while the remaining segments preferably have a Durometer of about 40. Additional information on the construction of the catheter 12, e.g., its material composition, its size and shape, may be found in co-pending applications Ser. Nos. 08/730,327 and 08/730,496, both filed on Oct. 11, 1996, and in PCT Application No. PCT/IUS97/01459, filed on Jan. 31, 1997, the disclosures of which are expressly incorporated herein by reference.

The catheter 12 also includes a lumen 32 which extends from an entry port 52 in the handle 50 to a tip member 44 on the distal portion 30 for receiving an imaging element, preferably an intravascular ultrasound ("IVUS") device (not shown) therein. An orientation element is provided, preferably a marker "cage" structure 16 formed from a plurality of elongate members or struts 38, 40, on the distal portion 30 located distally of the peripheral opening 34. The struts 38, 40 preferably extend distally from the distal end 26 substantially parallel to the longitudinal axis 22 to the proximal edge 42 of the tip member 44, thereby further defining the IVUS lumen 36. The struts 38, 40 preferably define a peripheral window 46, which may be covered by a material substantially transparent to the imaging element or may remain open to blood flow. The struts 38, 40 are preferably substantially rigid members, such as wires or hypotubes, which are reflective to the imaging element, i.e., will produce a reflection or artifact when the imaging element is operated, and/or may be substantially opaque to an external imaging apparatus (not shown). In a preferred form, the struts 38, 40 may be formed from a radiopaque material, such as platinum or tantalum.

Preferably, the struts 38, 40 have an asymmetrical configuration about the periphery 20 that has a predetermined relationship with the location of the peripheral opening 34. More preferably, a first strut 38 is located on the periphery 20 directly distally from the location of the peripheral opening 34. A pair of struts 40 are then positioned opposite the first strut 38, thereby defining an isosceles triangle cross-sectional configuration, with the first bar 38 at the top of the triangle. Thus, the cage structure 16 may "point" circumferentially towards the location of the peripheral opening 34 on the periphery 20, i.e., towards the location from which a guidewire may be deployed.

Alternatively, the orientation element may include one or more externally visible markers (not shown) placed at one or more predetermined locations on the periphery 20 of the catheter 12, or markers placed in conjunction with the cage structure 16. The markers, which may be provided from a radiopaque material, may define a pattern to facilitate detection of the orientation of the distal portion 30 about the longitudinal axis 22 with the aid of an external imaging apparatus (not shown). Although the catheter device 10 may include both internally viewable markers (such as the cage structure 16) and externally visible markers on the catheter 12, preferably only one marker or orientation element is necessary to effectively orient the peripheral opening 34. Further discussion of systems and methods for orienting a catheter device 10, e.g., regarding use of an IVUS device or radiopaque markers, fluoroscopy and the like, may be found in U.S. application Ser. No. 09/048,147, filed Mar. 25, 1998, the disclosure of which is expressly incorporated herein by reference.

The tip member 44 attached to the struts 38, 40 has an annular shape formed from a substantially flexible material to further define the lumen 32. The tip member 44 is preferably tapered to facilitate insertion into and direction along the lumen of a blood vessel or other body passage, and is substantially coaxial with the lumen 32 in the catheter 12 to facilitate the introduction of a guidewire, rail or other instrument axially therethrough.

Figure 6A:
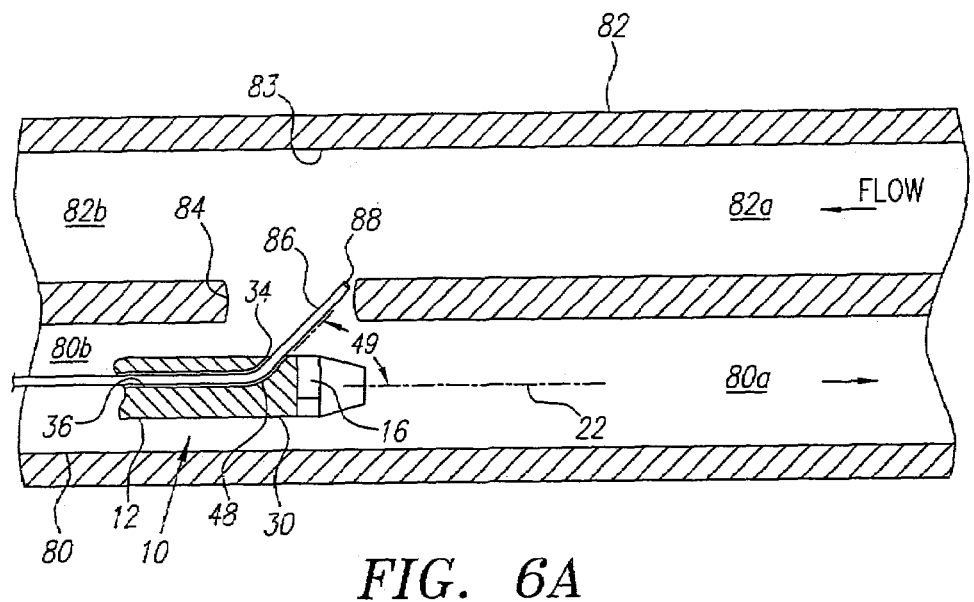
FIGS. 6A and 6B are cross-sectional views showing the catheter device of FIG. 1A being used to direct a guidewire between two adjacent blood vessels.

The catheter device 10 may be used in a method for directing a guidewire between adjacent body passages through an interstitial channel or branch, preferably in a predetermined direction. For example, as shown in FIG. 6A, the catheter device 10 may be used to direct a guidewire 86 from a first blood vessel 80 upstream into an adjacent second blood vessel 82. The distal portion 30 of the catheter 12 is percutaneously introduced into a patient's body, e.g., within the venous system, and advanced to a location within the first vessel 80, preferably a coronary vein, until it is adjacent to an interstitial channel 84, which extends substantially transversely to the second vessel 82, preferably a coronary artery.

The catheter 12 is oriented within the first vessel 80 to orient the peripheral opening 34 towards the interstitial channel 84, for example, using an IVUS device (not shown) to orient the cage structure 16 and identify the circumferential location of the peripheral opening 34. Alternatively, one or more radiopaque or other externally visible markers (not shown) on the distal portion 30 may be viewed using fluoroscopy and the like to facilitate orientation.

Once properly oriented, a guidewire 86 is advanced distally through the guidewire lumen 36 until it contacts the deflecting ramp 48, and exits the peripheral opening 36 substantially laterally with respect to the longitudinal axis 22. Because the deflecting ramp 48 has an acute deflection angle 49, the guidewire 86 is directed through the interstitial channel 84 towards the upstream portion 82a of the second vessel 82, and consequently, as the guidewire 86 enters the second vessel 82, it is directed into the upstream portion 82a of the second vessel 82.

Figure 6B:
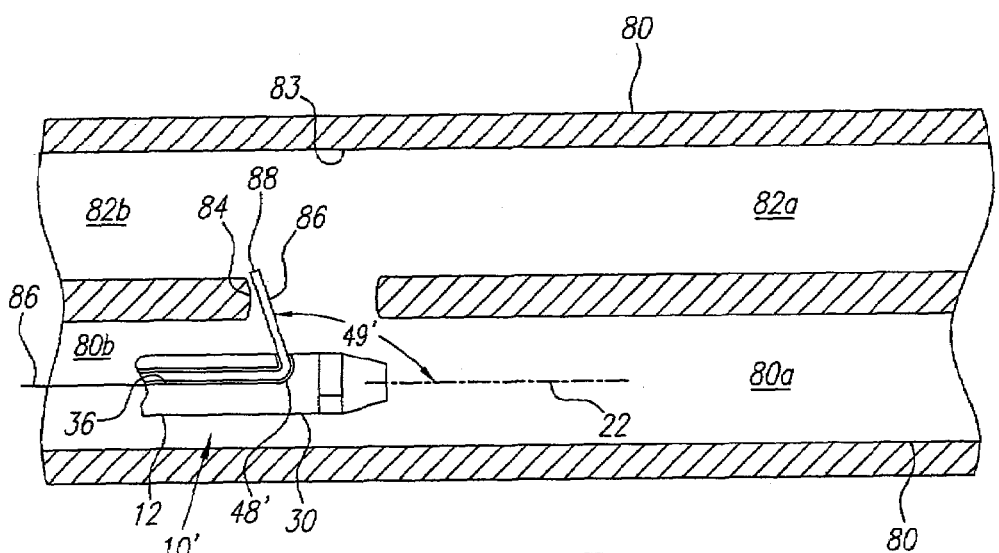

Alternatively, as shown in FIG. 6B, it may be desirable to direct a guidewire 86 into a downstream portion 82b of the second vessel 82. A catheter device 10', having a deflecting ramp 48' with an oblique deflection angle 49', such as the distal portion 30' shown in FIG. 1C, may be advanced into the first vessel 80 until properly positioned and oriented adjacent the interstitial channel 84. When the guidewire 86 is advanced through the guidewire lumen 36, it contacts the deflecting ramp 48', thereby directing the guidewire 86 towards and into the downstream portion 82b of the second vessel 82.

In a further alternative, the catheter 12 may be directed into the first vessel 80 to a selected location without a pre-existing interstitial channel. The catheter 12 may be oriented with respect to the adjacent second vessel 82, and the guidewire 86 advanced towards the second vessel directly through the intervening tissue. Thus, the guidewire 86 may have a sufficiently small and pointed tip and may be sufficiently rigid to puncture through the tissue from the first vessel into the second vessel without having to create an interstitial channel in advance.

Turning to FIGS. 2A-2H, a second preferred embodiment of a catheter device 110 is shown that is similar to the catheter device 10 previously described, but also includes a needle assembly 114 which is deployable from a peripheral opening 134 communicating with a needle lumen 136 similar to the guidewire lumen 36 previously described. The catheter device 110 includes an elongate catheter 112 defining a circumference or periphery 120, a longitudinal axis 122 between its proximal and distal ends 124, 126, a proximal portion 128 having a handle 150 and a distal portion 130 having a size and shape to facilitate insertion into a blood vessel. The needle lumen 136 extends from a needle entry port 154 in the handle 150 to the peripheral opening 134 in the distal portion 130, and includes a deflecting element or ramp 148 therein adjacent to the peripheral opening 134 having a deflection angle 149.

The handle 150 is preferably a substantially rigid member including an entry port 152, the needle entry port 154, and a needle lumen flush port 156 in communication with the needle lumen 136. The ports 152, 154 and 156 may include one or more seals to prevent backflow, as will be appreciated by those skilled in the art. A control and/or locking mechanism 158 is located on the handle 150 that includes a needle thumb slide 168 and an adjustable needle stop 170 that cooperatively slide along a graduated region 160 of the handle 150.

The needle thumb slide 168 may be directed axially along the graduated region 160 to deploy the needle assembly 114, as described more particularly below. The adjustable needle stop 170 is slidable on the handle 150 and is securable at a plurality of positions on the graduated region 160 of the handle 150. Thus, the adjustable needle stop 170 may be locked at a first position on the graduated region 160, loosened, directed axially to a second position on the graduated region 160, and locked at the second position to limit the movement of the needle thumb slide 168, and consequently the depth of penetration of the needle assembly 114.

With particular reference to FIGS. 2D-2H, the needle assembly 114 includes an elongate tubular body 163 having a puncturing distal tip 164 and a bushing/bearing assembly 166. During assembly or prior to use, the distal tip 164 may be inserted into the needle entry port 154 and directed distally through the needle lumen 136 until the bushing/bearing assembly 166 engages the needle thumb slide 168 on the handle 150. The needle thumb slide 168 is coupled with the needle assembly 114, for example, with ball plungers or detents (not shown) in the handle 150, for fixing axial movement of the needle assembly 114 to the needle thumb slide 168.

The needle assembly 114 includes a guidewire lumen 172 extending from the bushing/bearing assembly 166 to an outlet 174 in the distal tip 164. In one preferred form, shown in FIG. 2E, the distal tip 164 has a standard bevel 180 such that the outlet 174 is oriented in a substantially distal direction. Alternatively, the distal tip 164 may have a reverse bevel 180' such that the outlet 174' is oriented in a substantially proximal direction, as shown in FIG. 2F. In another alternative, shown in FIGS. 2G and 2H, the distal tip 164 may include a deflection ramp 182 within the guidewire lumen 172 and the outlet 174 may be provided on the periphery of the distal tip 164 adjacent the deflection ramp 182 for directing a guidewire (not shown) substantially distally beyond the distal tip 164. In a further alternative, the needle assembly 114 and/or the distal tip 164 may be formed from a shape memory alloy, such as Nitinol, that is precurved to enhance lateral deployment of the distal tip 164. The precurved shape of the distal tip 164 may be selected and set to direct a guidewire substantially laterally in a predetermined direction with respect to the longitudinal axis 122.

In still another alternative, the needle assembly 114 may have a solid distal tip (not shown), and a side opening may be provided at a predetermined location on the periphery of the needle assembly 114 proximate the distal tip. The side opening may communicate with the guidewire lumen 172 and may be provided at a proximal, distal or transverse location on the periphery as desired.

Figure 6C:
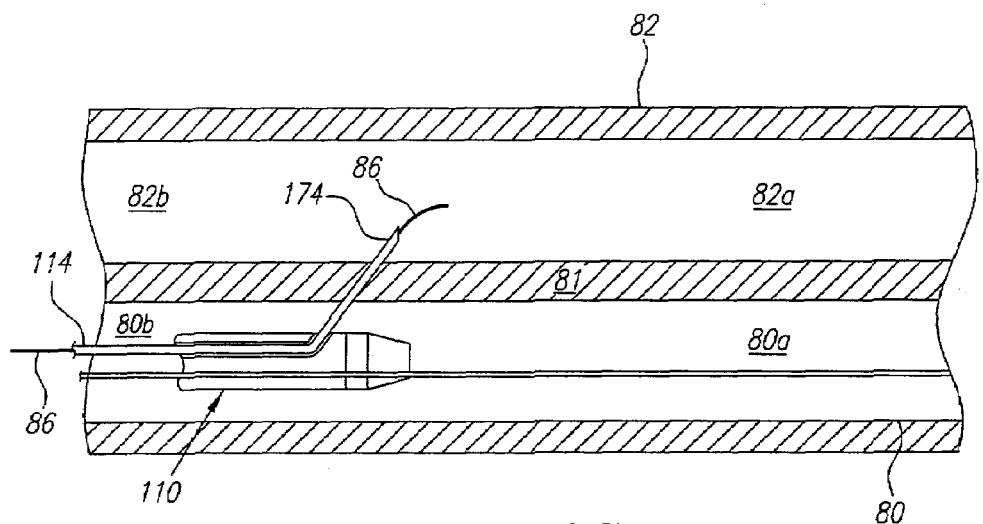
FIG. 6C is a cross-sectional view showing the catheter device of FIG. 2A being used to direct a guidewire between two adjacent blood vessels.

During use, as shown in FIG. 6C, the catheter device 110 may be advanced into a first blood vessel 80 to a selected location adjacent a second blood vessel 80. The distal portion may be positioned and/or oriented using an IVUS device and/or radiopaque markers similar to those described above. In addition, the IVUS device may be used to assess the site of an interstitial channel between the first and second vessels 80, 82. For example, the IVUS device may. facilitate the identification of side branches in the vessels, and/or sites of plaque or lesions which may be inappropriate for the channel location. The identification of side branches may be particularly important to ensure that vessels downstream of the channel are not starved by blood preferably flowing into side branches immediately adjacent the channel rather than downstream into the desired vessel.

Once the distal portion 130 is properly positioned and oriented, the needle assembly 114 may be advanced distally. Because of the deflecting ramp 148 and/or the precurved shape of the distal tip 174, the distal tip 174 is directed substantially laterally out of the peripheral opening 134, penetrating through the tissue 81 between the first and second vessels 80, 82, and into the second vessel 82.

A guidewire 86 may then be advanced through the guidewire lumen 172 within the needle assembly 114 and directed out the outlet 174 in the distal tip 164. The standard bevel 180 of FIG. 2E or the deflecting ramp 182 of FIGS. 2F and 2G preferably direct the guidewire 86 substantially laterally and distally, i.e., towards an upstream portion 82a of the second vessel 82. Other interventional devices (not shown) may then be advanced over the guidewire 86 through the tissue 81, for example, to create an interstitial channel (not shown) between the vessels 80, 82, and/or to perform an intervention in the first and/or second vessels 80, 82. Alternatively, if desired, the guidewire 86 may be directed substantially laterally and proximally, i.e., towards a downstream portion 82b of the second vessel 82, for example, by providing the reverse bevel 180' on the distal tip 164, as shown in FIG. 2F, a deflecting ramp that is oriented substantially proximally (not shown) and/or a substantially obliquely precurved shape (not shown) for the distal tip 164, as will be appreciated by those skilled in the art.

Figure 3A:
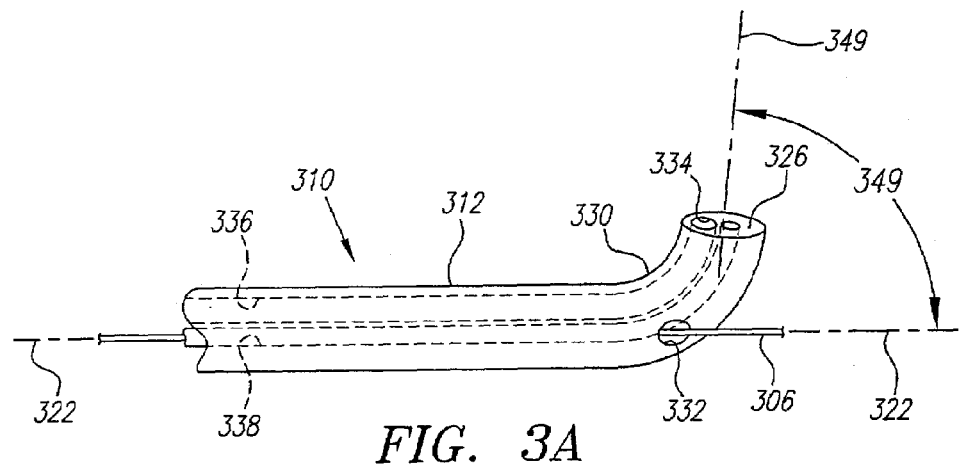
FIG. 3A is a side view of a precurved distal portion of a catheter, in accordance with the present invention, being delivered over a guidewire.
Figure 3B:
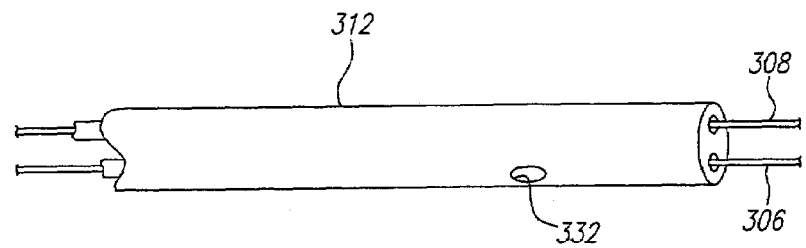
FIG. 3B is a side view of the distal portion of the catheter of FIG. 3A, with a stiffening element received through the catheter to straighten the precurved distal portion.
Figure 6D:
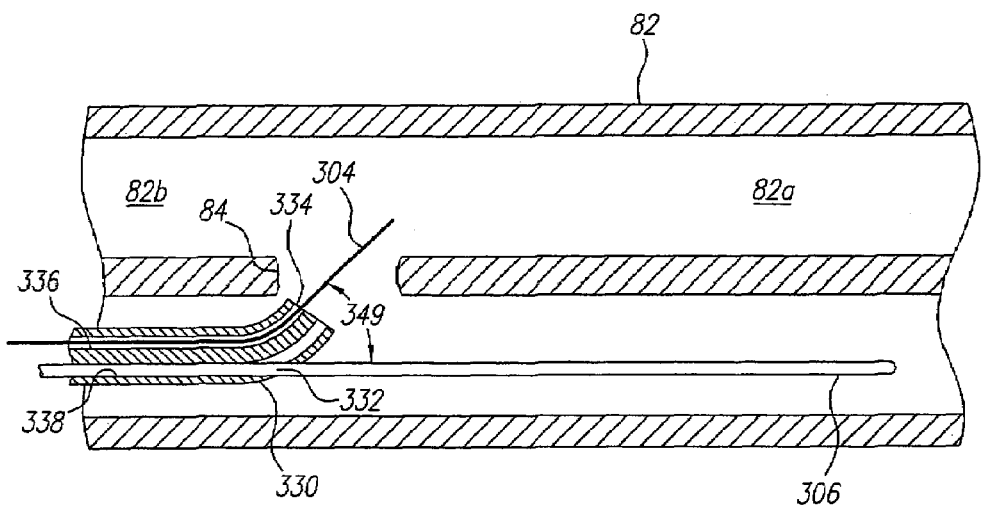
FIG. 6D is a cross-sectional view showing the catheter device of FIGS. 3A and 3B being used to direct a guidewire between two adjacent blood vessels.

In a third preferred embodiment, shown in FIGS. 3A, 3B and 6D, a catheter device 310 for directing a guidewire may be provided that has a precurved distal portion 330, e.g., the distal portion 330 may have a shape memory or otherwise may be biased to adopt a curved shape defining a predetermined angle 349 with respect to the longitudinal axis 322. The catheter device 310 preferably includes a catheter 312 having first and second lumens 336, 338 for receiving guidewires therethrough that extend from a proximal end (not shown) to a distal end 326 of the catheter 312. The second lumen 338 may include a peripheral opening 332 on an outer surface of the catheter 312, as shown in FIG. 3B.

During use, a stiffening member, such as a first guidewire 308, may be directed into the first lumen 336 to substantially straighten out the distal portion 330 parallel to a longitudinal axis 322 (see FIG. 3B). The catheter device 310 may then be percutaneously introduced into the vasculature, preferably over a second guidewire 306 already in place, and advanced until the distal portion 330 is in a first vessel 80 adjacent an interstitial channel or side branch 84 (FIG. 6D). The distal portion 330 may be oriented with respect to the interstitial channel 84, for example, using the imaging and/or orientation elements (not shown) previously described.

The first guidewire 308 may then be at least partially withdrawn from the first lumen 336, and the second guidewire 306 may also be withdrawn from the second lumen 338, such that the distal portion 330 automatically adopts its curved shape. The second guidewire 306 may then be advanced distally until it exits the second lumen 338 out the peripheral opening 332, or alternatively, the second guidewire 306 may be completely removed from the body. If left in place, the second guidewire 306 may be used to substantially anchor the curved distal portion 330 adjacent the interstitial channel 84 and/or may be used for introducing subsequent devices (not shown).

As shown particularly in FIG. 6D, a third guidewire 304 may then be advanced through the first lumen 332 until it exits the distal opening 334 and enters the interstitial channel 84. Preferably, the curved shape defines an angle 349 with respect to the longitudinal axis 322 that is substantially acute to direct the third guidewire 304 substantially laterally and distally towards an upstream portion 82a of the second vessel 82. Alternatively, the distal portion 330 may define a substantially oblique angle (not shown) if it is desired to direct the guidewire 304 substantially laterally and proximally towards the downstream portion 82b of the second vessel 82.

The second guidewire 306 may then be withdrawn from the distal portion 330 (if not already removed), and the catheter 310 may then be advanced over the third guidewire 304 into the interstitial channel 84. The distal portion 330 may then be reoriented with respect to the upstream portion 82a, and the third guidewire 304 may be withdrawn from the distal portion 330, whereupon the distal portion 330 may adopt its curved shape such that the distal end 326 is oriented towards the upstream portion 82a of the second vessel 82. A fourth guidewire (not shown) may then be advanced through one of the lumens in the catheter 310 and directed into the upstream portion 82a of the second vessel 82. The catheter 310 may then be withdrawn, and one or more devices may then be advanced over the fourth guidewire, for example, to perform an intervention at a location between the upstream portions 80b and 82a, and/or to further direct a guidewire within the patient.

Figure 3C:
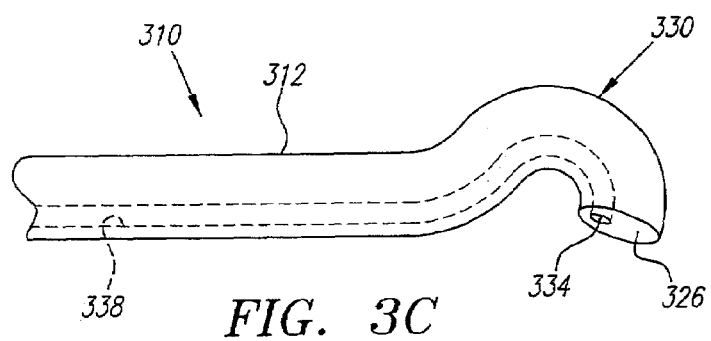
FIG. 3C is a side view of an alternative embodiment of a catheter with a "C" shaped precurved distal portion.
Figure 4:
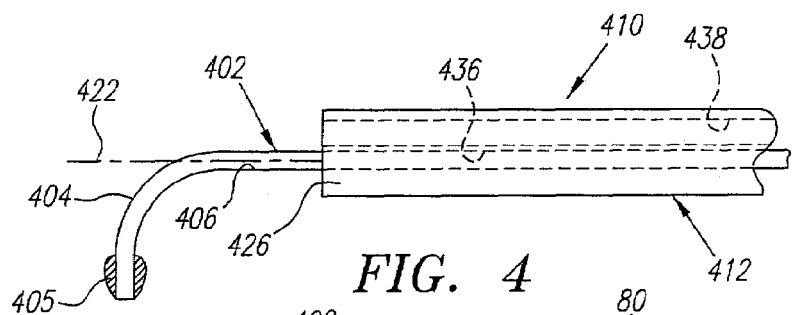
FIG. 4 is a side view of a channel finding device, including a precurved catheter deployable from an outer sleeve.

Alternatively, after the distal portion 330 is advanced into the interstitial channel 84, the distal portion 330 may be oriented towards the downstream portion 82b, and a guidewire directed downstream into the second vessel 82. In further alternative configurations, such as that shown in FIG. 3C, the distal portion 330' of the catheter 310' may be precurved into a substantially "C" or other curved shape or into an "S" shape (not shown) which may be advanced into the interstitial channel 84 and/or the second vessel 82 to facilitate directing a guidewire in a selected direction without needing subsequent deployment of another guidewire from within the interstitial channel 84.

In a preferred form, the radius of curvature of the distal portion 330 is substantially larger than the diameter of the vessel, such that the distal portion 330 may favor advancing into side branches, such as an interstitial channel. In an alternative form, the distal portion may be deflectable by a pullwire to facilitate creation of a predetermined curved shape, such as that disclosed in co-pending application Ser. No. 08/730,327, filed Oct. 11, 1996, the disclosure of which is expressly incorporated herein by reference.

Figure 17:
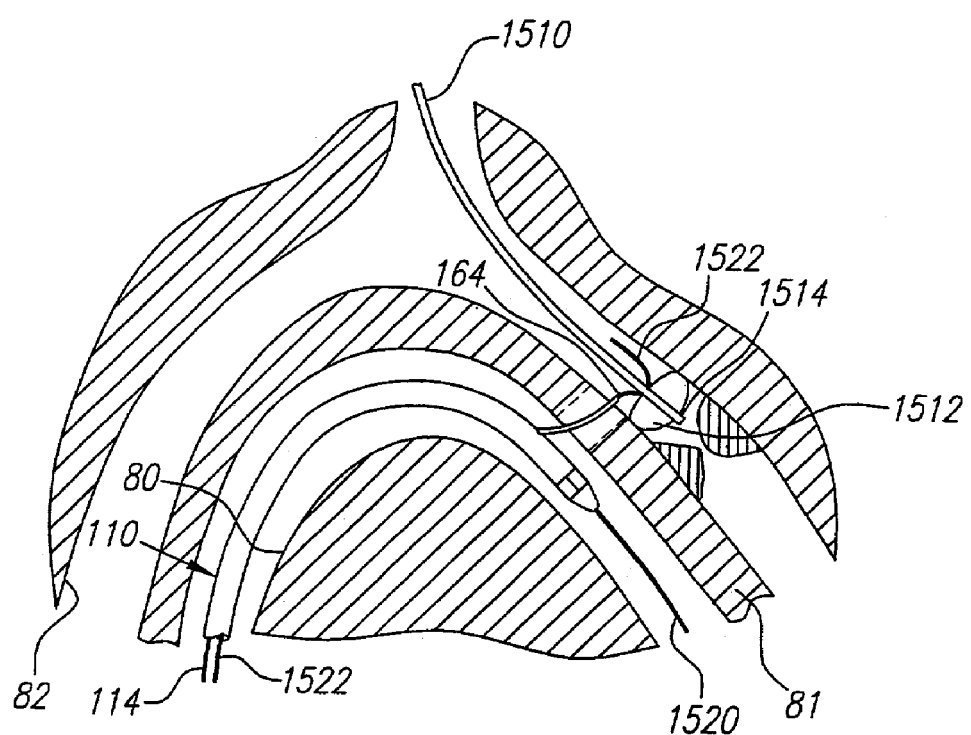
FIG. 17 is a cross-section view of a deflecting device being used to deflect a guidewire from an undesired portion of a blood vessel.

To further facilitate directing a guidewire, a deflecting member may be provided within a target vessel to prevent a guidewire from being directed into an undesired portion of the vessel. For example, as shown in FIG. 17, the deflecting member is preferably a balloon catheter 1510 having an inflatable balloon 1512 on its distal end 1514. The distal end 1514 of the balloon catheter 1510 may be advanced into a vessel until the balloon 1512 is positioned in an undesired portion of the vessel.

The balloon 1512, or other deflecting element, may be activated, e.g., by inflating the balloon, until it substantially engages the walls of the vessel, thereby blocking the undesired portion from receiving a guidewire therethrough. When a guidewire 1522 is subsequently advanced into the vessel, if it is inadvertently directed towards the undesired portion, it will contact the balloon 1512 and be deflected back towards a desired portion of the vessel.

More preferably, as shown in FIG. 17, the distal end 1514 of the balloon catheter 1510 may be advanced into a coronary artery 82 adjacent to a stenotic region 83 prior to the direction of a guidewire 1522 into the artery 82 from an adjacent coronary vein 80. Once properly positioned, the balloon 1512 may be inflated until it engages the wall of the artery 82. A wire directing device, such as the catheter device 110 of FIG. 2A, may be introduced into the coronary vein 80 proximate the stenotic region 83 in the artery 82, e.g., over a guidewire 1520.

A needle tip 164 of a needle assembly 114 may be advanced from the catheter device 110 through interstitial tissue 81 and/or through an interstitial channel 84 (shown in phantom) into the artery 82. The guidewire 1522 may then be deployed from a lumen (not shown) within the needle assembly 114 into the artery 82, or directly from a catheter device without a needle assembly, such as the catheter device 10 of FIG. 1A. The guidewire 1522 may freely enter an upstream portion of the artery 82 away from stenotic region 83. If the guidewire is directed towards the stenotic region 83, however, the guidewire 1522 may be deflected by the balloon 1512, as shown in FIG. 17, back towards the upstream portion of the artery 82.

In a further preferred embodiment shown in FIGS. 4, and 5A-5D, a channel finding device 410 is provided that includes an outer catheter or sleeve 412 having first and second lumens 436, 438. A relatively small diameter catheter or tubular member 402, having a curved distal portion 404 terminating in an atraumatic tip 405, is insertable through one of the lumens 436 of the outer sleeve 412. The first lumen 436 and the atraumatic tip 405 may have relative diameters that prevent the atraumatic tip 405 from being withdrawn fully within the first lumen 436.

The tubular member 402 is preferably formed from a shape memory material, e.g., Nitinol, having a relatively small diameter, e.g., about 0.010-0.040 inch, and preferably about 0.0180-0.0260 inch. The tubular member 402 includes a lumen 406 extending between its proximal end (not shown) and the atraumatic distal tip 405, having a relatively small diameter, i.e., just sufficiently large to pass a guidewire therethrough, e.g., about 0.010-0.038 inch, and preferably about 0.014 inch.

Figure 5A:
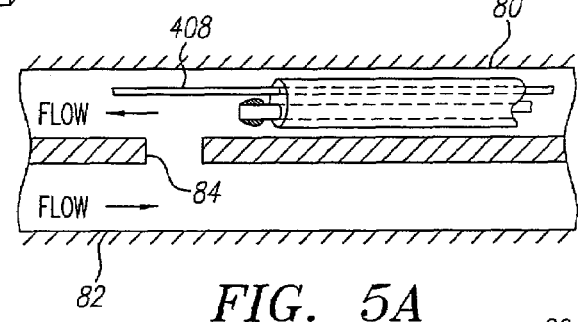
FIGS. 5A-5D are cross-sectional views of a method of directing a guidewire between adjacent blood vessels using the channel finding device of FIG. 4.
Figure 5B:
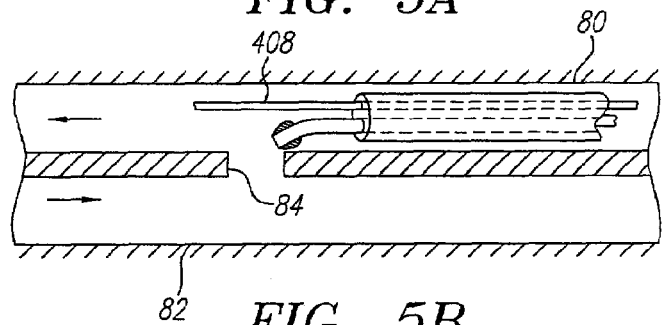

Prior to introduction into a patient's body, the tubular member 402 is placed within the first lumen 436 of the outer sleeve 412 such that the atraumatic tip 405 is adjacent the distal end 426 of the outer sleeve 412, thereby substantially straightening out the curved distal portion 404. The outer sleeve 412, with the tubular member 402 therein, may be percutaneously introduced into a patient, preferably within their vasculature, and advanced over a first guidewire 408 into a first vessel 80 adjacent to an interstitial channel 84 communicating with a second vessel 82 (FIG. 5A). Once positioned and/or oriented within the first vessel 80, the tubular member 412 may be advanced distally out of the outer sleeve 402 (FIG. 5B). The curved distal portion 404 may extend substantially laterally with respect to a longitudinal axis 422 of the outer sleeve 402, thereby favoring any branches, e.g., the interstitial channel 84, extending substantially laterally from the first vessel 80.

Figure 5C:
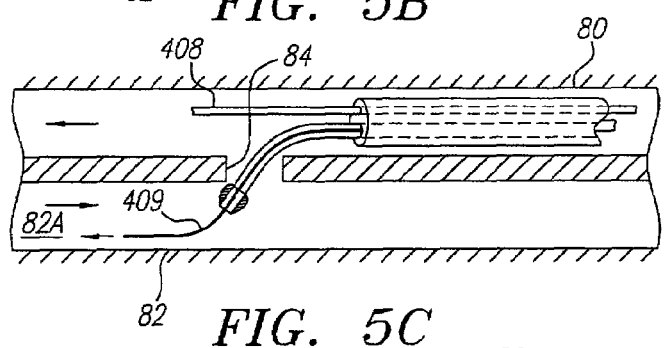
Figure 5D:
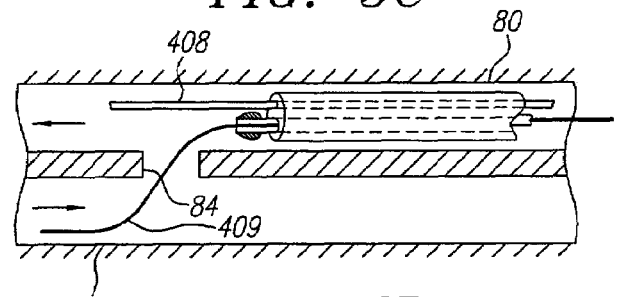

As the tubular member 412 is advanced distally, it may "pop" into the interstitial channel 84 and be directed at least partially through the interstitial channel 84 towards the second vessel 82. A second guidewire 409 may then be advanced through the lumen 406 and out the atraumatic tip 405 into the second vessel 82, preferably towards an upstream portion 82a (FIG. 5C). Once the second guidewire 409 is advanced sufficiently into the second vessel 82, the tubular member 412 may be withdrawn back into the first lumen 436 of the outer sleeve 402 (FIG. 5D). The channel finding device 410 may then be withdrawn from the vasculature, leaving the second guidewire 409 in place between the first and second vessels 80, 82 over which subsequent devices (not shown) may be advanced.

Figure 16:
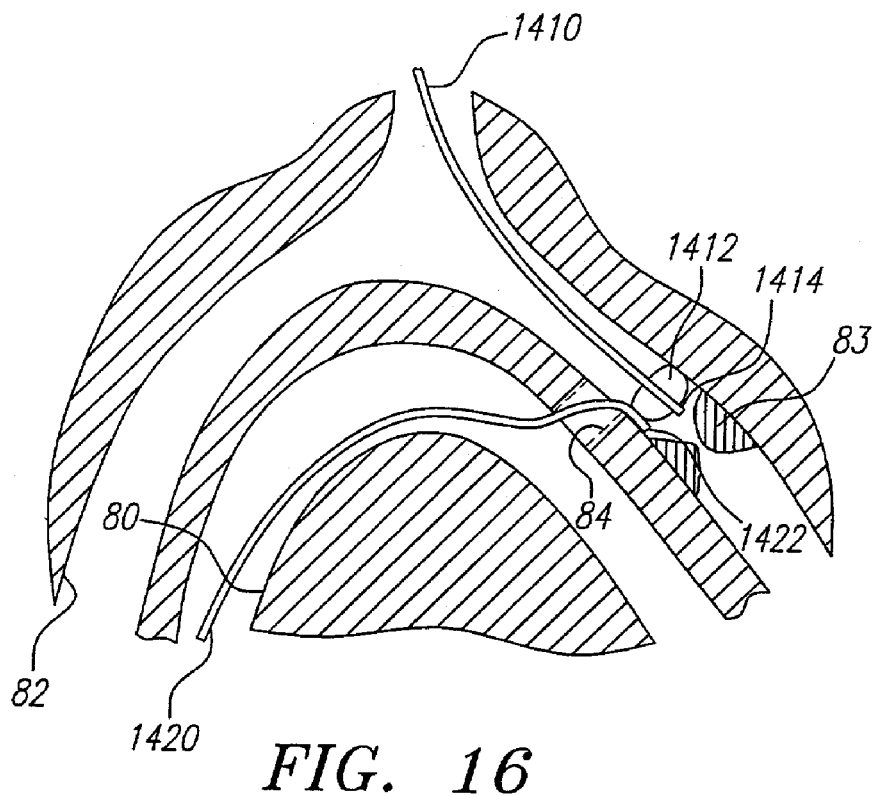
FIG. 16 is a cross-sectional view of a stabilization device being used to secure a guidewire in a selected location within a blood vessel.

In a second aspect of the present invention, stabilization devices may be provided to substantially secure a target guidewire in a selected location once placed there. For example, as shown in FIG. 16, a balloon catheter 1410 may be provided with a balloon 1412 on its distal end 1414 that is expandable between contracted and enlarged conditions. The balloon 1412 or the balloon catheter 1410 may have one or more passages (not shown) therethrough to allow perfusion across the balloon 1412. Alternatively, an expandable basket may be provided instead of the balloon 1412 that is capable of detachably engaging a guidewire or other rail.

With the balloon 1412 in its contracted condition, the distal end 1414 of the balloon catheter 1410 may be advanced to a selected location, e.g., within a coronary artery 82, where a target guidewire 1420 has been previously directed. The balloon 1412 may then be expanded to the enlarged condition to substantially engage the wall of the vessel 82, thereby substantially securing the distal end 1422 of the guidewire 1420 between the balloon 1412 and the wall of the vessel 82. Other interventional devices (not shown) may be subsequently advanced and/or withdrawn over the guidewire 1420 with the guidewire 1420 substantially maintained in place.

The balloon catheter 1410 may prevent the guidewire 1420 from being inadvertently pulled out of the selected location of the vessel 82 when a device is subsequently advanced over the guidewire 1420 or from being accidentally advanced beyond the selected location, where it may damage the vessel 82. Alternatively, the guidewire itself may have an inflatable tip (not shown), e.g. a balloon attached on its distal tip, that may be expanded to engage the wall of the vessel and stabilize the guidewire in place at the selected location.

As shown in FIG. 16, the balloon catheter 1410 may be particularly useful for stabilizing a guidewire placed through an interstitial channel 84 between a coronary vein 80 and a coronary artery 82 immediately adjacent to a stenotic region 83. For example, because of side branches (not shown) extending from the vessels or other conditions within the vessels, it may necessary to provide the channel 84 in close proximity to the stenotic region 83. Thus, the distal end 1422 of the guidewire 1420 may be directed through the channel 84 only a relatively short distance towards the stenotic region 83, e.g., about 1 cm, which may increase the risk of the guidewire 1420 being withdrawn back through the channel 84 when other devices (not shown) are directed over the guidewire 1420.

To substantially prevent this, the balloon catheter 1410 may be advanced into the artery 82 adjacent to the distal end 1420, and inflated to secure the distal end 1420 between the balloon 1412 and the wall of the artery 82. Other devices may be advanced over the guidewire 1420 to complete a procedure, and then the balloon 1412 may be deflated and the balloon catheter 1410 withdrawn from the artery 82.

Figure 8A:
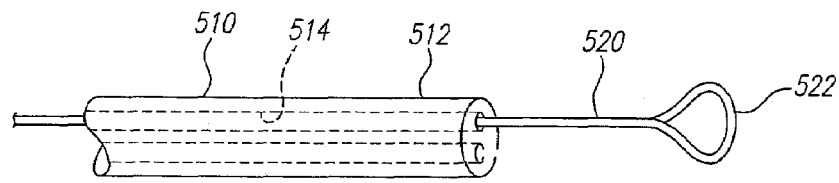
FIGS. 8A and 8B are perspective views of single and double lumen snare catheters, respectively.

In another aspect of the present invention, systems and methods are provided for snaring and/or manipulating, e.g., by releasably securing, grasping or coupling, a guidewire within a body passage, preferably to direct the guidewire between adjacent blood vessels within a patient's vasculature. Turning to FIG. 8A, a single lumen snaring catheter 510 is shown that has a proximal end (not shown), a distal end 512 having a size adapted for insertion into a blood vessel, and a lumen 512 extending between the proximal and distal ends 512. A snare 520 is provided in the lumen 514 that is deployable from the distal end 512 of the snaring catheter 510 and that includes a loop 522 adapted to assume a substantially circular or elliptical shape.

Figure 8B:
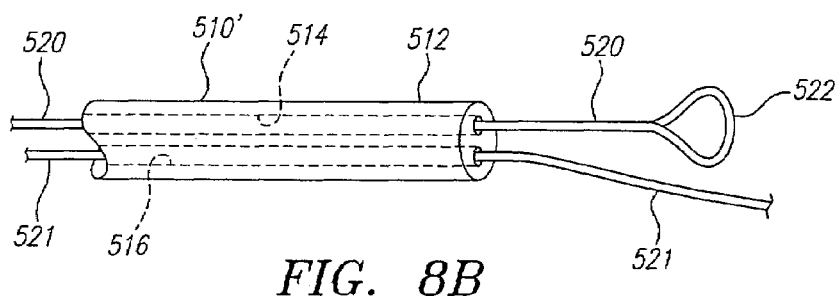

Preferably, the loop 522 has a cross-section similar to the diameter of a body passage, e.g., a blood vessel, into which the snare 520 may be deployed, and may be biased to expand substantially transversely across the body passage to facilitate capturing a guidewire or other rail in the loop 522. More preferably, as shown in FIG. 8B, the snaring catheter 510' also includes a second lumen 516 for receiving a guidewire 521 therethrough, over which the snaring catheter 510 may be advanced into the lumen.

The snaring catheter 510 may also include imaging and/or orientation elements, such as the IVUS device and/or radiopaque markers (not shown) previously described. The snaring catheter 510 may be incorporated into a method for snaring, manipulating and/or releasing one or more guidewires, such as the methods of directing a guidewire between two adjacent vessels connected by an interstitial channel described further below.

In a preferred form, the snaring catheter may have a specially configured composite structure, including a substantially rigid proximal portion and a flexible tapered distal portion (not shown). The proximal portion may be formed from a hypotube or other substantially rigid tubular member, e.g., having a length of about forty five inches. The distal portion may be formed from duel lumen tubing, e.g., Pebax tubing having a Durometer of between about 63-70. One of the lumens may receive a snaring device therethrough, while the other lumen may receive a guidewire therethrough to facilitate advancement of the snaring catheter over the guidewire.

Figure 15A:
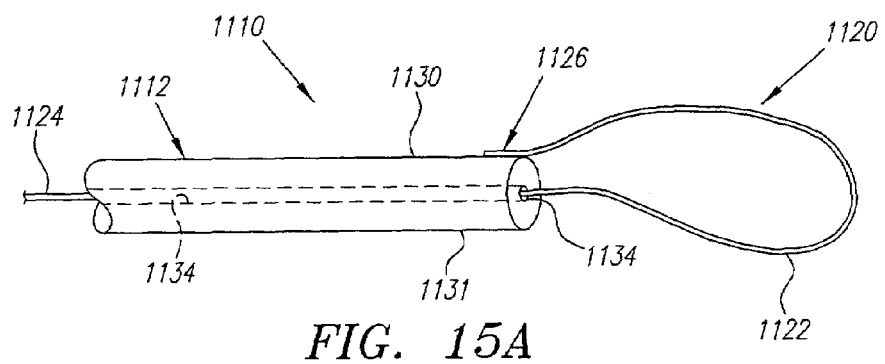
FIGS. 15A-15C are perspective views of alternative embodiments of a snaring device deployable from a single lumen.

In further alternatives, the snaring catheter may have a snaring wire that is partially fixed to the distal end of the catheter, i.e., one end of the snaring member may be attached to the catheter, while the other end remains free to controllably define a loop for capturing a guidewire device. For example, in FIG. 15A, a distal portion 1130 of a snaring catheter 1110 is shown that includes a catheter body 1112 and a snaring wire 1120 defining a loop 1122. A first end 1126 of the snaring wire 1120 is attached to a distal end 1131 of the catheter body 1112 adjacent to an outlet 1134 of a lumen 1136. A second end 1124 of the snaring wire 1120 extends proximally through the lumen 1136 to provide a control wire. When the second end 1124 is directed distally, the loop 1122 is enlarged to thereby facilitate capture of a guidewire device (not shown) therein, and when the second end 1124 is directed proximally, the loop 1122 may be used to substantially secure the guidewire device to the distal end 1131.

Figure 15B:
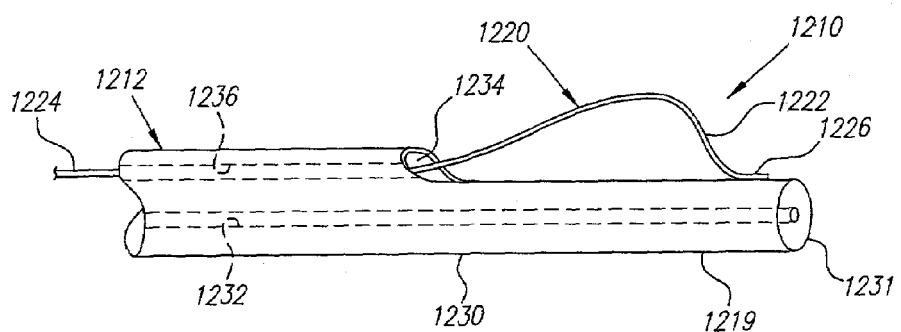

Alternatively, as shown in FIG. 15B, a catheter body 1212 may be provided having a lumen 1236 with an outlet 1234 located a short distance proximate its distal end 1231. Optionally, a second lumen 1232 (shown in phantom) may be provided to facilitate advancement of the snaring catheter 1210 over a guidewire (not shown). A first end 1226 of a snaring wire 1220 is attached to the distal end 1231, and a second end 1224 is slidably disposed within the lumen 1236. In this form, a guidewire device (not shown) may be captured with the snaring wire 1220 and secured to an outer surface 1219 of a distal portion 1230 of the snaring catheter 1210, thereby substantially reducing risk of the guidewire device being pulled into the lumen 1136.

Figure 15C:
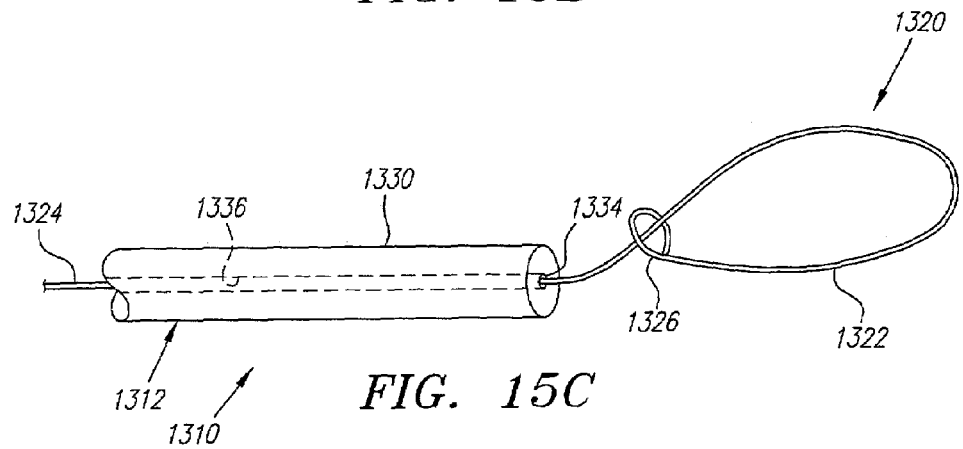

In a further alternative, shown in FIG. 15C, a snaring catheter 1310 may include a lassolike snaring member 1320 deployable from a lumen 236 extending through a distal portion 1330 of a catheter body 1312. A first end 1324 of the snaring member 1320 extends proximally through the lumen 1336, while a second end 1326 is looped around itself to provide a closable loop 1322 for capturing a guidewire device (not shown). The distal portion 1330 of the catheter body 1312 may be synchable, i.e., after deployment of the loop 1322 from the lumen 1336, the outlet 1334 may be substantially closed to prevent the loop 1322 and/or the guidewire device captured in the loop 1322 from being drawn into the lumen 1336.

In an alternative embodiment, the snare may be deployable substantially laterally, for example from the catheter device 110 of FIGS. 2A-2H. The lumen 172 of the needle assembly 114 may be sufficiently large to accommodate a snare (not shown), such as those described above. Thus, a snare may be deployed from the distal tip 164 of the needle assembly 114 in a manner similar to the method of directing a guidewire previously described.

Figure 13A:
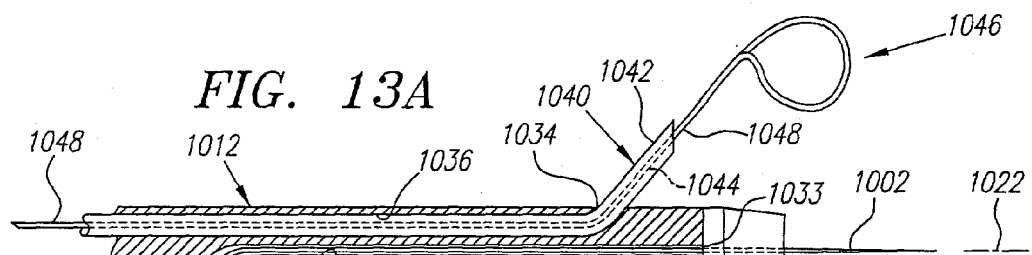
FIGS. 13A and 13B are cross-sectional views of alternative embodiments of a proximal lumen snaring device, including a laterally deployable sleeve from which a snare may be deployed.

In a further embodiment, shown in FIG. 13A, a snare 1046 may be deployable from a needle device 1040, which is in turn deployable substantially laterally from a catheter device 1010, similar to the catheter device 110 of FIGS. 2A-2H.

Figure 18A:
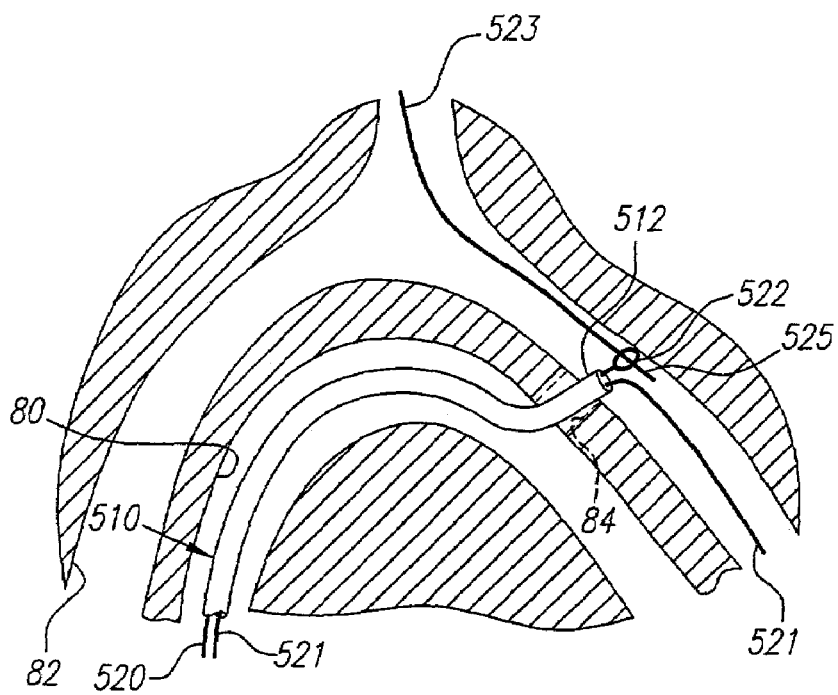
FIGS. 18A and 18B are cross-sectional views showing a method for snaring and directing a guidewire between two adjacent blood vessels.
Figure 18B:
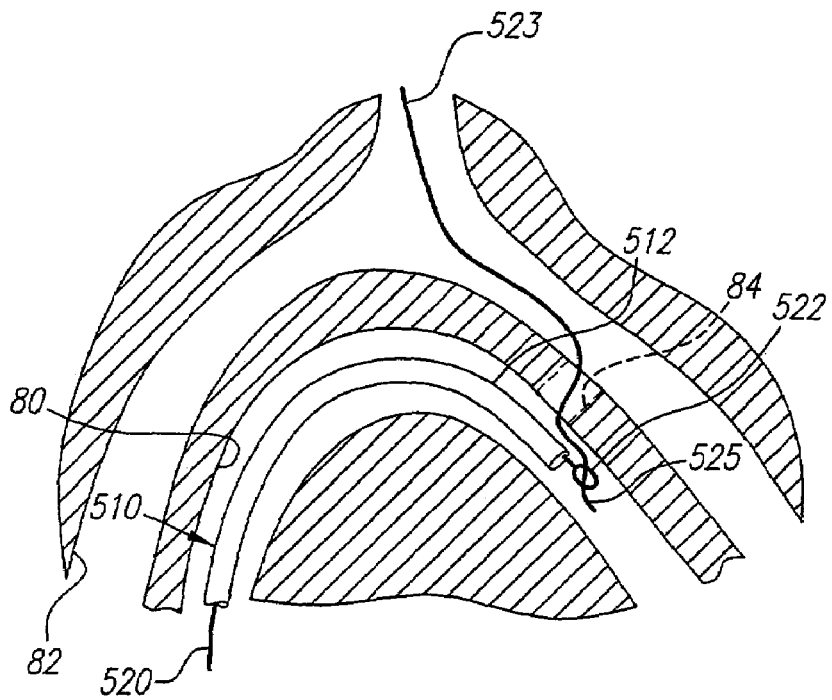

Turning now to FIGS. 18A and 18B, a snaring catheter 510, such as that shown in FIG. 8B, may be used to snare, direct and release a guidewire 523 within a patient's vasculature, preferably between a coronary artery 82 and a coronary vein 80 via an interstitial channel 84. The snaring catheter 510, with the loop 522 of the snare 520 within the lumen 514, may be percutaneously introduced into the patient's vasculature and the distal end 512 advanced over a guidewire 521 through the coronary vein 80 to a first location, preferably within the coronary artery 82, where the target guidewire 523 or other rail has been previously placed. The snare 520 may be deployed from the distal end 512, and a distal end 525 of the target guidewire 523 may be captured within the loop 522 (FIG. 18A). The snare 520 may then be withdrawn back into the lumen 514, thereby also pulling the distal end 525 of the target guidewire into the lumen 514 and substantially securing it therein (not shown). Alternatively, if the channel 84 is near a stenotic region or other lesion (not shown), the snare 520 may be deployed prior to advancement of the target guidewire 523 into the artery 82. Once the loop 522 is properly positioned, the guidewire 523 may be advanced into the artery 82 until the distal end 525 is received in the loop 522.

The snaring catheter 510 may then be directed to a second location, preferably back through the channel 84 into the coronary vein 80. The guidewire 521 may be withdrawn from within the snaring catheter 510, and the snaring catheter 510 further manipulated within the coronary vein 80, thereby directing the target guidewire 523 to the second location. The snare 520 may be redeployed and the distal end 525 of the target guidewire 523 released from the loop 522 at the second location (FIG. 18B). The snare 520 may be withdrawn into the lumen 514, and the snaring catheter 510 withdrawn from the second location, leaving the target guidewire 523 in place (not shown). The target guidewire 523 may provide a rail over which one or more devices may be advanced, e.g., to provide access between the first and second locations, or the target guidewire 523 may be further manipulated prior or subsequent to performing an intervention.

Figure 19A:
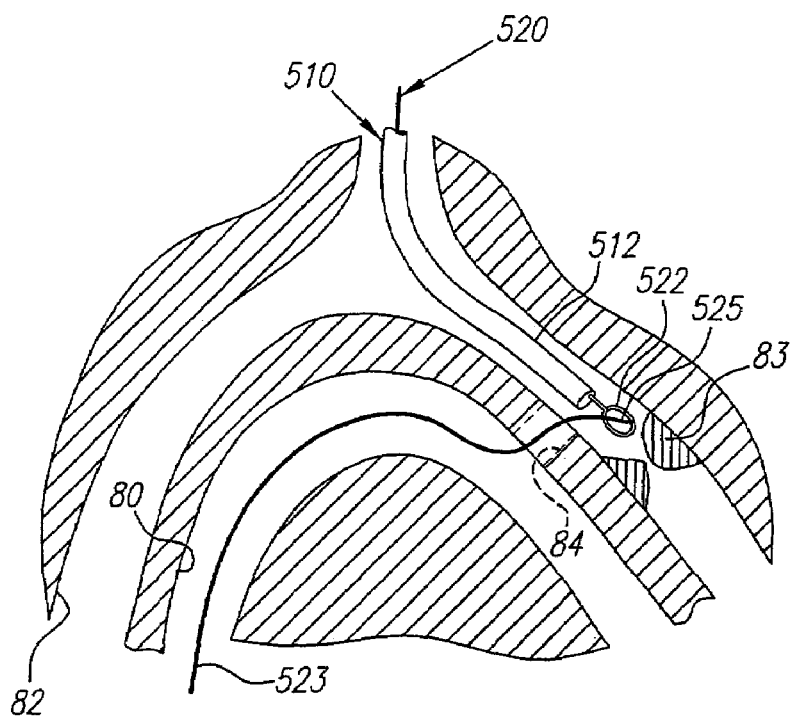
FIGS. 19A and 19B are cross-sectional views showing a method for delivering a guidewire between two adjacent blood vessels.
Figure 19B:
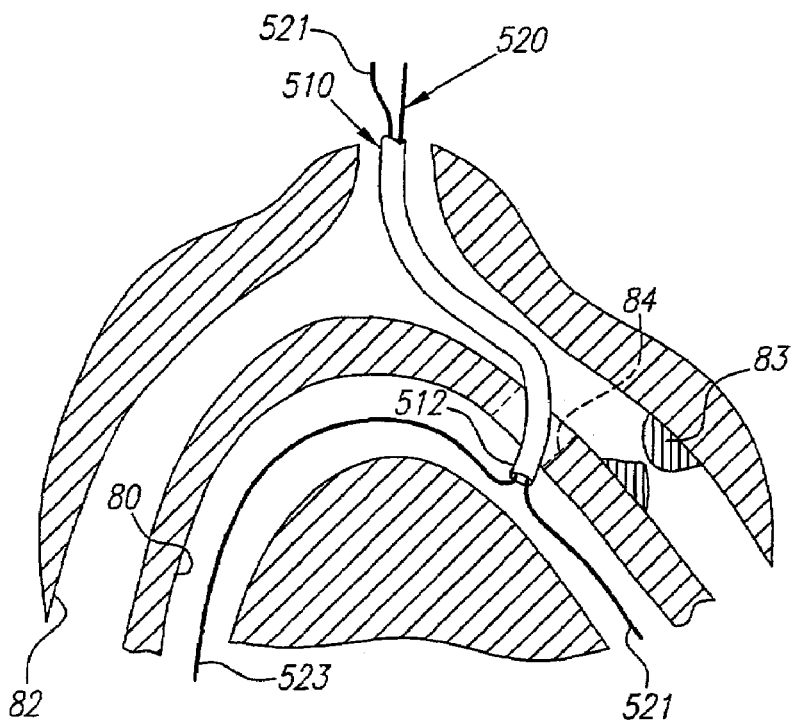

In a further alternative shown in FIGS. 19A and 19B, the snaring catheter 510 may be advanced into the artery 82, and the loop 522 of the snare 520 deployed adjacent the interstitial channel 84. The target guidewire 523 may then be directed from the vein 80 through the channel 80 into the loop 52 (FIG. 19A), which may then be used to secure the distal end 525 of the guidewire 523. The target guidewire 523 may then be withdrawn back through the channel 84 into the vein 80, thereby pulling the distal end 512 of the snaring catheter 510 through the channel 84 into the vein 80. A guidewire 521 may then be advanced through a lumen (not shown) in the snaring catheter and out the distal end 512 into the vein 80 (FIG. 19B). The snare 520 may be redeployed to release the target guidewire 523, and the snaring catheter 510 and target guidewire 523 may be withdrawn, leaving the artery-to-vein guidewire 521 in place. This method of snaring and releasing a guidewire may be particularly useful when the interstitial channel 84 is located immediately adjacent a lesion 83, which may prevent a guidewire from being stabilized within the artery prior to being snared, as previously described.

In another aspect of the present invention, an autotensioning handle or other control mechanism may be provided on a proximal end of a snaring catheter, such as those previously described, and particularly those embodiments having a snare deployable from a single lumen. For example, it may be desirable to control the tension applied to a snare to minimize the risk of damaging the snare or a target guidewire captured by the snare when they are withdrawn into the snaring catheter. In addition, because it may be desirable to releasably secure a target guidewire with a snaring catheter, a control mechanism may be provided to substantially reduce the risk of substantially permanently entangling the snare and the target guidewire and/or permanently securing the target guidewire within the snaring catheter. This risk may be particularly problematic when the snare is manipulated manually because inconsistent tension may be applied to the snare by different users.

Figure 8C:
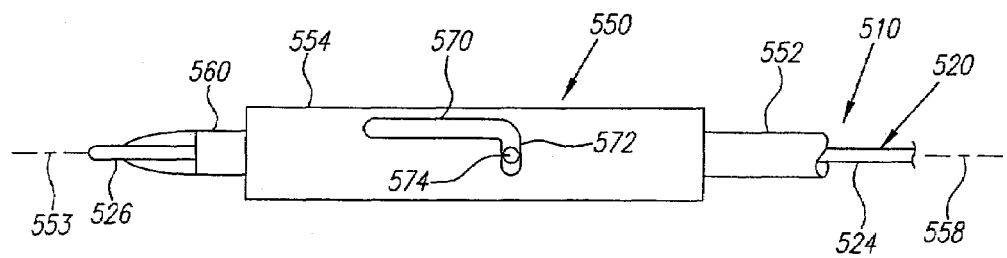
FIG. 8C is a side view of an autotensioning handle for a snaring catheter, such as those of FIG. 8A or 8B.
Figure 8D:
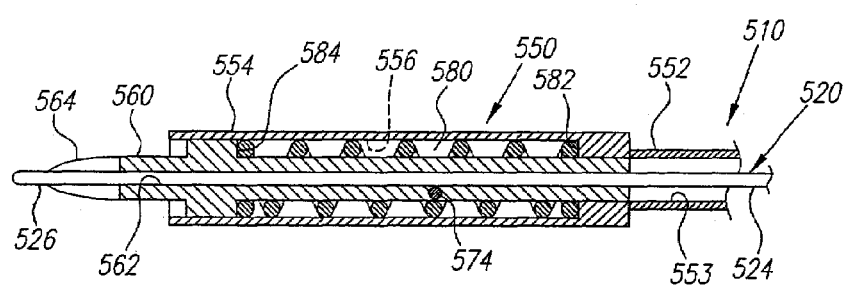
FIG. 8D is a cross-sectional view of the autotensioning handle of FIG. 8C.

Turning to FIGS. 8C and 8D, a preferred embodiment of an autotensioning handle 550 is shown attached to a proximal end 552 of a snaring catheter 510, which may be a device similar to any of the snaring devices described herein. The handle 550 includes an outer housing 554 defining an axial cavity 556 therein that extends along a longitudinal axis 558. A slidable member 560 is received in the axial cavity 556 that includes a snare lumen 562 extending between a collet 564 or other locking mechanism and a lumen 553 in the proximal end 552 of the snaring catheter 510. The snare lumen 562 has a size for accommodating a control wire 524 of a snare 520 therethrough, and the collet 564 may detachably secure a proximal end 526 of the control wire 524.

Preferably, the outer housing 554 includes an elongate slot 570 therethrough that extends substantially parallel to the longitudinal axis 558 for slidably receiving a thumb slide or control tab 574 that extends radially from the slidable member 560. The elongate slot 570 and control tab 574 thereby slidably cooperate to limit the travel of the slidable member 560 within the outer housing 554. A transverse slot 572 is also provided at one end of the elongate slot 570 for securing the control tab 574 in a distal or advanced position with respect to the longitudinal axis 558. Optionally, one or more additional transverse slots (not shown) may be provided for securing the control tab 572 in a proximal or withdrawn position and/or an intermediate position.

The outer housing 554 preferably contains a biasing mechanism for biasing the slidable member 560 towards the withdrawn or advanced position. For example, a helical spring 580 may be provided within the axial cavity 556 between the outer housing 554 and the slidable member 560 for automatically withdrawing the snare 520 into the snaring catheter 510 (not shown in FIGS. 8C and 8D) during use, i.e., by biasing the slidable member 560 to the withdrawn position. The outer housing 554 and the slidable member 560 include radially protruding surfaces 582, 584, respectively, for substantially containing the spring 580 within the axial cavity 556 and for applying an axial biasing force between the slidable member 560 and the outer housing 554.

Prior to use, a snare 520 may be advanced through the snare lumen 562 of the slidable member 560 and the lumen 553 of the snaring catheter 510 until a loop or other snaring element on the distal end (not shown) of the snare 520 is positioned adjacent the distal end (not shown) of the snaring catheter 510 within the lumen 553. The control wire 524 of the snare 520 may be axially fixed with respect to the slidable member 560 by securing the proximal end 526 of the control wire 524 to the collet 564 while the spring 580 is substantially relaxed, i.e., while the slidable member 560 is preferably in the withdrawn position.

Thereafter, the control tab 574 may be directed distally towards the advanced position to deploy the loop of the snare 520 out the distal end of the snaring catheter 510. The control tab 574 may be secured in the advanced position by sliding it transversely into the transverse slot 572, thereby preventing the loop from being withdrawn back into the snaring catheter 510 prematurely. Once a target guidewire, rail or other device is captured in the loop, the control tab 574 may be directed transversely from the transverse slot 572 back into the elongate slot 570. The spring 580 may then automatically direct the slidable member 560 back to the withdrawn position, and thereby withdraw the loop, with the target guidewire captured therein, into the lumen 553 of the snaring catheter 510.

The length and/or compression strength of the spring 580 may be preselected to provide a predetermined tension on the snare 520 when the control tab 574 is directed from the transverse slot 572 into the elongate slot 570. Thus, the loop and target guidewire may be pulled into the snaring catheter 510 in a controlled and substantially consistent manner that may facilitate subsequent redeployment of the snare 520 to release the target guidewire at another location within the patient's body, e.g., after further manipulation of the snaring catheter 510.

Figure 7A:
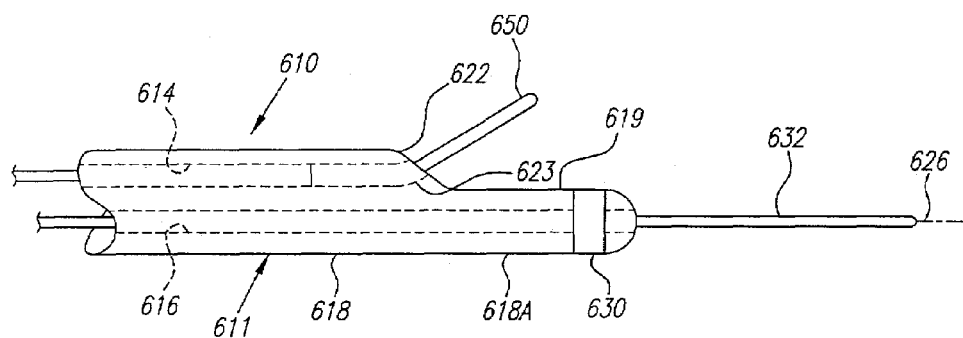
FIG. 7A is a side view of a dual lumen catheter for directing a guidewire laterally.
Figure 7B:
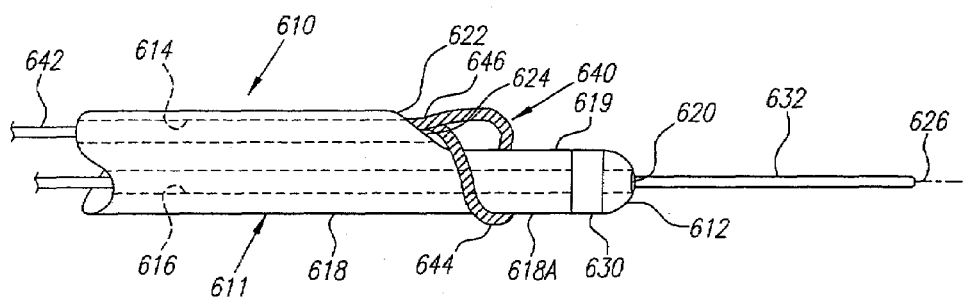
FIG. 7B is a perspective view of a dual lumen snaring catheter including a snare disposed about a distal portion of the snaring catheter.

Turning to FIG. 7B, another preferred embodiment of a snaring catheter 610 is shown that includes an elongate member or catheter body 611 having a proximal end (not shown), a distal end 612, a first lumen 614 and a second lumen 616 extending substantially between the proximal and distal ends 612. Preferably, a distal portion 618 of the catheter body 611 includes an angled step 624 such that the distal portion 618 tapers to a relatively narrow distal portion 618a adjacent the distal end 612.

A first outlet or peripheral opening 622, communicating with the first lumen 614, is located on the angled step 624, although alternatively the first outlet 622 may be located at another location proximal to the distal end 612 and/or on an outer surface 618 of the distal portion 618 (not shown). The first lumen 614 may also include a deflecting ramp 623 (FIG. 7A) adjacent the first outlet 622 for directing a guidewire, rail or other member deployed from the first lumen 614 substantially laterally with respect to a longitudinal axis 626 of the snaring catheter 610. Thus, the distal portion 618 with angled step 624 may also be used as a guidewire directing catheter, similar to those described above.

The second lumen 616 extends through the tapered distal portion 618a and terminates at a second outlet or distal opening 620 in the distal end 612, and preferably has a diameter adapted to receive a guidewire 632 therethrough. In addition, to facilitate viewing and/or positioning of the distal portion 618, a marker 630 may be provided at a predetermined location on the catheter body 611, for example, on the narrow distal portion 618a adjacent to the distal end 612. The marker 630 may be a simple annular shaped radiopaque band as shown in FIG. 7B. Alternatively, one or more specially configured markers (not shown) may be provided in a predetermined relationship with the first outlet 622 to facilitate orienting the first outlet 622, similar to the orientation elements previously described.

The snaring catheter 610 also includes a snaring member 640 including an elongate control wire 642 terminating in a loop 644 on its distal end 646. The snaring member 640 is slidably received in the first lumen 614 such that the loop 644 extends distally from the first outlet 622 and substantially surrounds the narrow distal portion 618a of the catheter body 611. The snaring member 640 may be directed proximally and distally such that the loop 644 substantially engages and disengages, respectively, the outer surface 619 of the distal portion 618 of the catheter body 611.

Preferably, the loop 644 is biased to assume an enlarged substantially circular or elliptical configuration, e.g., by forming the loop 644 from a shape memory alloy, such as Nitinol. More preferably, in the enlarged configuration, the loop 644 defines a predetermined diameter corresponding to a diameter of a lumen of a blood vessel into which the snaring member 640 may be deployed, with the narrow distal portion 618a of the catheter body 611 having a diameter substantially smaller than the predetermined diameter.

Thus, the distal portion 618 of the snaring catheter 610 may be percutaneously introduced into the vasculature and advanced over a guidewire 632 to a selected location, e.g., within a blood vessel, where a target guidewire may be placed. During introduction, proximal tension may be maintained on the control wire 642 such that the loop 644 substantially engages the outer surface 619 to minimize risk of the loop 644 inadvertently catching on any body structures or objects therein, which may damage the snare and/or the body structures.

Once in position, the control wire 642 may be directed distally, whereupon the loop 644 may expand into its enlarged configuration, preferably substantially across the lumen of the vessel. The loop 644 in its enlarged configuration may be used to capture a distal end of the target guidewire, which may require additional manipulation of the snare 640 and/or the target guidewire. The control wire 642 may then be pulled proximally to substantially engage the loop 644, and the target guidewire captured by the loop 644, against the outer surface 619 of the snaring catheter 610.

The snaring catheter 610 may then be directed within the vasculature, e.g. into a second blood vessel, where it may be desired to direct the target guidewire. The control wire 642 may then be directed distally, releasing the distal end of the target guidewire from engagement with the outer surface 619 of the snaring catheter 610. Thus, the snaring catheter 610 may more effectively facilitate capture and subsequent release of a target guidewire or other rail, substantially eliminating the risk of permanently securing the target guidewire within a lumen of the snaring catheter, or damaging the target guidewire tip.

Figure 9A:
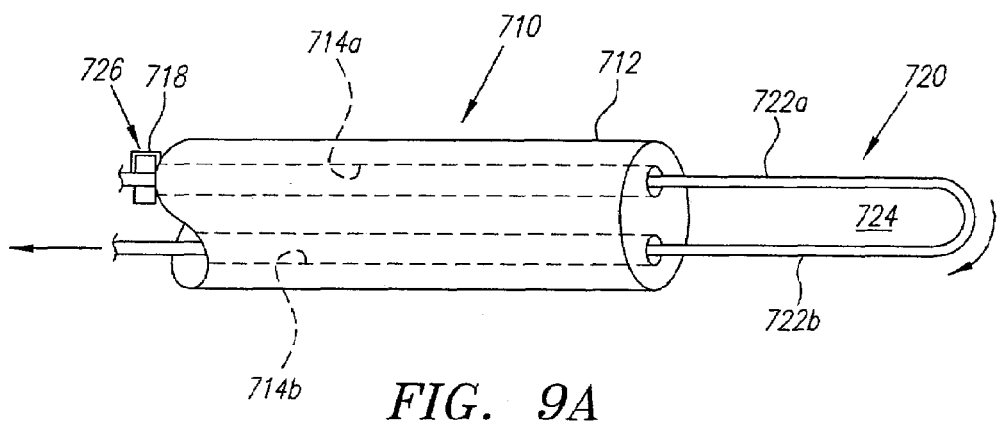
FIGS. 9A and 9B are perspective views of alternative embodiments of a dual lumen and a tri lumen snare catheter, without and with a guidewire lumen, respectively.
Figure 9B:
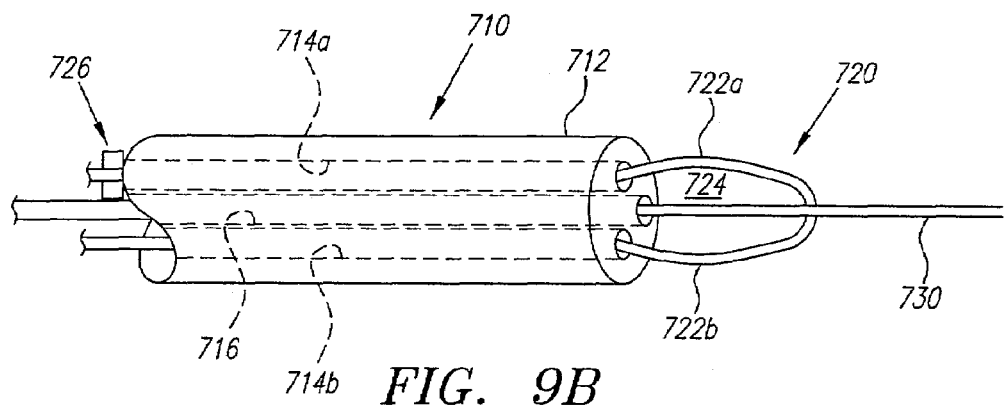

Turning to FIGS. 9A and 9B, another preferred embodiment of a snaring catheter 710 is shown that includes first and second snare lumens 714a, 714b for receiving first and second ends 722a, 722b of a snare 720, respectively, to thereby define a loop region 724 for capturing a target guidewire or other rail. Optionally, as shown in FIG. 9B, the snaring catheter 710 may also include a guidewire lumen 716 to allow introduction of the snaring catheter 710 over a guidewire 730.

The first snare end 722a includes a tab, enlarged hub or other member for substantially preventing the first snare end 722a from being pulled distally through the first snare lumen 714a beyond a corresponding enlarged region 718 of the first snare lumen 714a. Thus, to enlarge or contract the loop region 724, the second end 722b may be directed distally or proximally, respectively. Alternatively, the first snare end 722a may be allowed to travel freely within the first snare lumen 714a, and one or both ends 722a, 722b may be directed distally and proximally to enlarge or contract the loop region 724.

The snaring catheter 710 may then be used similar to the previous embodiments to capture a target guidewire and direct the target guidewire to another location within the vasculature. Because the loop region 724 is defined by the ends of the snare being placed through separate snare lumens, a target guidewire captured by the loop region is substantially secured against the distal end 712 of the snaring catheter 710, rather than being drawn into a lumen where the target guidewire may get irretrievably stuck. Thus, the snaring catheter 710 may allow repeated capture and release of one or more guidewires or rails to facilitate manipulation during complicated intraluminal or transvascular procedures.

In another form, a directing or snaring member and a target guidewire, catheter, rail or other guidewire device may include cooperating end effectors for detachably securing, coupling or capturing a distal portion of the target member to a distal end of the directing member. For example, as shown in FIGS. 10A, 10B, 10C and 10D, a directing catheter 810 may be provided that includes a grasping mechanism 816 on its distal end 812. The directing catheter 810 may include an outer catheter or sleeve 814, and the grasping mechanism 816 may be attached to one or more control wires 818 extending through the outer sleeve 814, such that the grasping mechanism 816 may be manipulated from the proximal end (not shown) of the directing catheter 810, e.g., to open and close the grasping mechanism 816. The directing catheter 810 may also include a guidewire lumen (not shown) to allow introduction of the directing catheter 810 over a guidewire into the first vessel 80.

The grasping mechanism 816 preferably has rounded or atraumatic tips to substantially minimize damage to the vessels or other tissue during use. In one preferred form shown in FIG. 10D, the grasping mechanism 816 includes cooperating jaws 815 that together define an aperture 817 for receiving a catheter or other rail, having a cross-section similar to a generally circular shape of the aperture 817. In another preferred form shown in FIG. 10E, the grasping mechanism 816 includes cooperating jaws 815' defining flat engagement surfaces 819 for securing a guidewire or other relatively small rail.

Preferably, the directing catheter 810 is directable substantially laterally with respect to its longitudinal axis 821. For example, the outer sleeve 814 or other portion of the directing catheter 810 may be steerable using one or more pullwires, may be precurved or may be deliverable substantially laterally from another device. Preferably, the directing catheter 810 includes a lumen (not shown) allowing the directing catheter 810 to be advanced over a guidewire (not shown) already in place through the channel.

A target catheter 820 is also provided that may include an enlarged distal tip 822 on its distal portion 824 to facilitate securing the distal portion 824 with the grasping mechanism 814. Preferably, the target catheter 820 is a relatively thin-walled, flexible catheter having a relatively small diameter, e.g., less than about 0.030-0.040 inch, and having a lumen 826 for receiving a guidewire 830 therethrough. Alternatively, it may not be necessary to provide the enlarged distal tip 822 on the target member 820 to securely grab the distal portion 824 with the grasping mechanism 814. In a further alternative, the enlarged distal tip 822 may be an expandable member (not shown), such as a balloon or a basket-like structure.

Figure 10A:
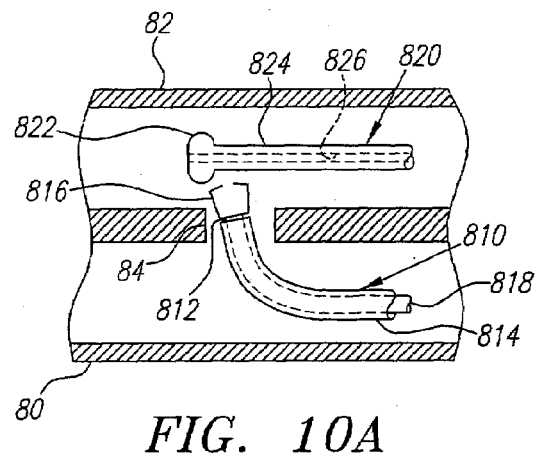
FIGS. 10A and 10B are cross-sectional views showing a system and method for directing a target catheter through a channel between adjacent vessels, including directing and target catheters having cooperating end effectors.
Figure 10B:
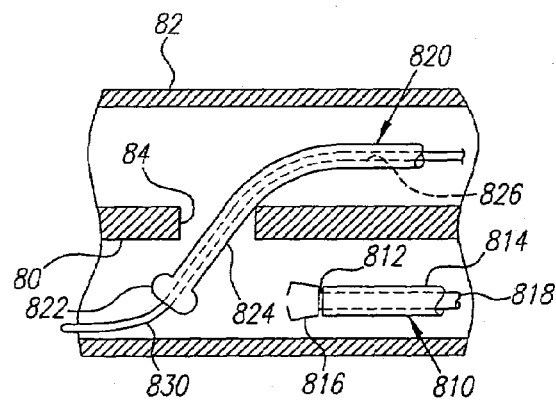
Figure 10D:
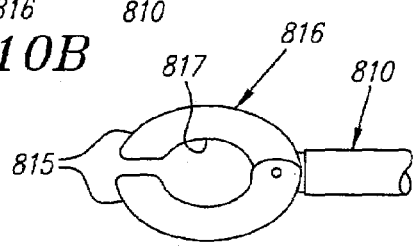
FIGS. 10D and 10E are side views of alternative embodiments of a grasping mechanism for the directing catheter of FIGS. 10A and 10B.
Figure 10C:
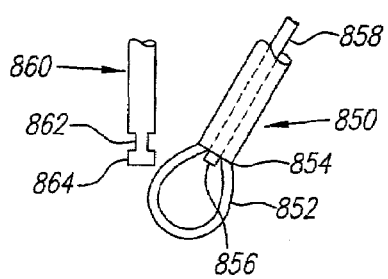
FIG. 10C is a side view of an alternative embodiment of cooperating effectors provided on a directing catheter and a target catheter similar to that shown in FIGS. 10A and 10B.
Figure 10E:
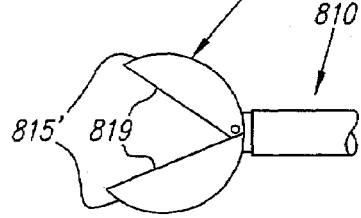

The directing catheter 810 and the target catheter 820 may be independently percutaneously introduced into a patient's body, preferably into the patient's vasculature, and advanced into first and second blood vessels 80, 82, preferably within a coronary artery and a coronary vein, respectively, adjacent to an interstitial channel 84, as shown in FIGS. 10A and 10B. The directing catheter 810 may be advanced through the channel 84 from the first vessel 80 into the second vessel 82. The grasping mechanism 814 may be directed to an open or release position, the distal portion 824 of the target catheter 820 may be captured therein, and the grasping mechanism may be directed to a closed or engaged position to secure the distal portion 824 therein.

The directing catheter 810 may then be withdrawn through the channel 84 back into the first vessel 80, thereby directing the distal portion 824 of the target catheter 820 into the first vessel 80. The distal portion 824 may be released from the grasping mechanism, and a guidewire 830 may be advanced through the lumen 826 out the distal portion 824 and into the first vessel 80 to place the guidewire 830 between the first and second vessels 80, 82 over which other devices may then be advanced. The target catheter 820 and/or the directing catheter 810 may then be removed from the first and second vessels leaving the guidewire 830 in place.

Alternatively, instead of the directing catheter 810 described, a snaring device similar to those previously described, e.g. having a deployable loop, may be provided for detachably securing a target guidewire or other rail that may or may not have an enlarged distal tip. In a further alternative, shown in FIG. 10C, a snaring member 850 may be provided that includes a loop 852 on its distal end 854, and a deployable pin 856 connected to a control wire 858 extending from the proximal end (not shown) of the snaring member 850. The corresponding target member 860 includes a recess 862 on its distal portion 864, that may have an annular shape or a shape similar to the pin 856.

The snaring member 850 and target member 860 may be introduced into two adjacent vessels, similar to the method previously described, and the snaring member 850 manipulated to receive the distal portion 864 within the loop 852. The pin 856 may then be deployed until it is received in the recess 862, thereby coupling the distal portion 864 to the snaring member 860. The snaring member 850 may thus be used to direct the target member 860 from one vessel into an adjacent vessel, e.g., where the target member 860 may be used to place a guidewire or other device through or over the target member 860. The pin 856 may be withdrawn from the recess 862 into the distal end 854 of the snaring member 850, and the distal portion 864 released from the loop 852.

In still another alternative, the directing member and/or the target member may be provided with one or more magnets or electromagnets (not shown) on their distal ends. The directing member and target member may be introduced into adjacent vessels having a channel communicating between them. The directing member may then be directed substantially laterally, e.g., into the channel, until a magnet on one of the members is attracted to a magnetic material or another magnet, on the other member. Once the directing and target members are magnetically coupled together, the target member may then be directed between the vessels as desired, by manipulating the directing member. The directing and target members may be mechanically releasable from one another, e.g., by a pin deployable from one of the members to push the magnet(s) apart. Alternatively, the member may electrically releasable, e.g., by simply turning off the electromagnet(s).

Alternatively, the directing member may include a basket assembly or other structure (not shown) on its distal end. The basket assembly may be deployable and/or expandable to receive the distal end of the target member between individual elements of the basket assembly and then withdrawn and/or contracted to capture the distal end of the target member in the basket assembly. A wire helix may alternatively be provided that is deployable from the directing member, e.g., a catheter, guidewire or other device, for capturing the target member.

In still another alternative, a target guidewire device, e.g., a catheter, may include a snare on its distal portion which may be introduced into a first vessel. A guidewire may be introduced into a second vessel, for example, from one of the catheter devices described previously, and directed substantially laterally through a channel between the vessels until a distal end of the guidewire is received in the snare. The guidewire may then be withdrawn back into the second vessel, thereby pulling the target guidewire device into the second vessel.

Figure 11A:
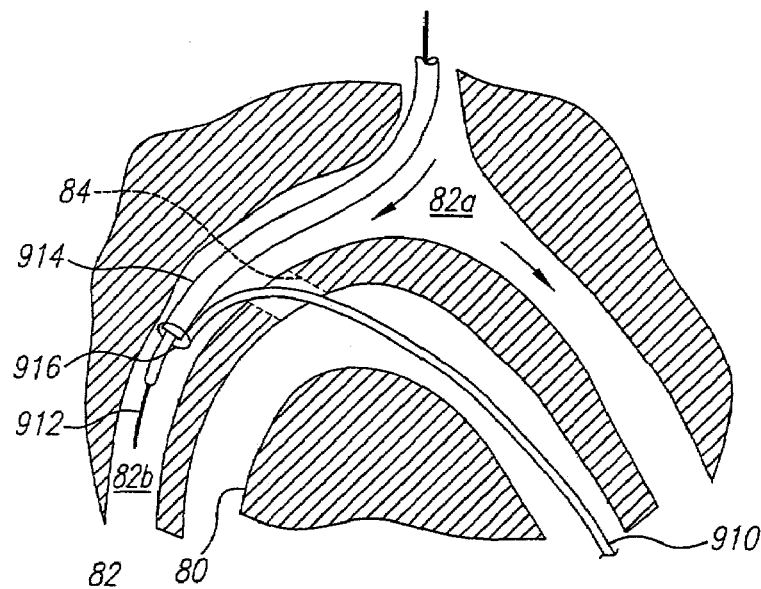
FIGS. 11A and 11B are cross-sectional views showing a method of placing a guidewire under tension through an interstitial channel and two adjacent blood vessels.
Figure 11B:
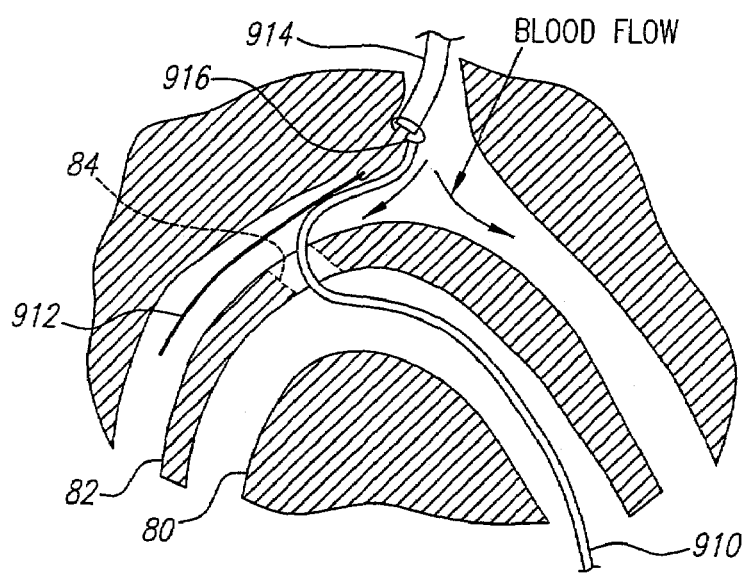

In another aspect of the present invention, a method for directing, positioning and/or manipulating one or more guidewires with respect to two adjacent vessels is provided. FIGS. 11A-11B show a method for "flossing" a first guidewire 910 between two adjacent vessels, i.e., for placing the first guidewire 910 under tension through an interstitial channel between two adjacent vessels. For example, the first guidewire may be "flossed" between one percutaneous entry point (not shown) through a first vessel 80, preferably a coronary vein as shown, through an interstitial channel 84, through a second vessel 82, preferably a coronary artery as shown, to a second percutaneous entry point (not shown). Alternatively, a catheter or other grasping mechanism may be used to hold the first guidewire from within one or both of the vessels. Thus, the first guidewire may be held under tension from outside the channel, e.g., by the direct application of force at two entry sites, or at one entry site and a grasping mechanism within a vessel.

The first guidewire 910 (a "vein-to-artery" or "v-to-a" guidewire) may be advanced into the first vessel 80 and directed through the channel 84 into a downstream portion 82b of the second vessel 82. For example, a catheter device (not shown in FIG. 11A), similar to those shown in FIGS. 1A-5D, may be percutaneously introduced into the first entry site and advanced into the first vessel 80 until adjacent to the channel 84. The first guidewire 910 may then be deployed substantially laterally and distally from the catheter device through the channel 84 and into the downstream portion 82*a* using one of the methods previously described.

A second guidewire 912 may be percutaneously introduced into the second entry site, and advanced through the coronary system into the second vessel 82. A snaring member 914, such as those shown in FIGS. 7A-10C, may be advanced over the second guidewire 912 into the second vessel 82, and then a snare or other grasping mechanism 916 may be deployed to capture the first guidewire 910 therein.

With the first guidewire 910 captured by the snaring member 914, the snaring member 814 may be withdrawn from the second vessel 82 and out of the body through the second entry site, thereby "flossing" the first guidewire 910 between the first and second entry sites.

Alternatively, the first guidewire 910 may be advanced into the first vessel 80 proximate the interstitial channel 84, but not directed through the channel 84. The snaring member 914 may be advanced from the second entry site into the second vessel 82, through the channel 84 into the first vessel 80, and the grasping mechanism may be used to capture the first guidewire 910. The snaring member 914 may then be withdrawn through the channel 84 and out of the second vessel 82, thereby pulling the first guidewire 910 into the second vessel 82 and out the second entry site.

Figure 2A:
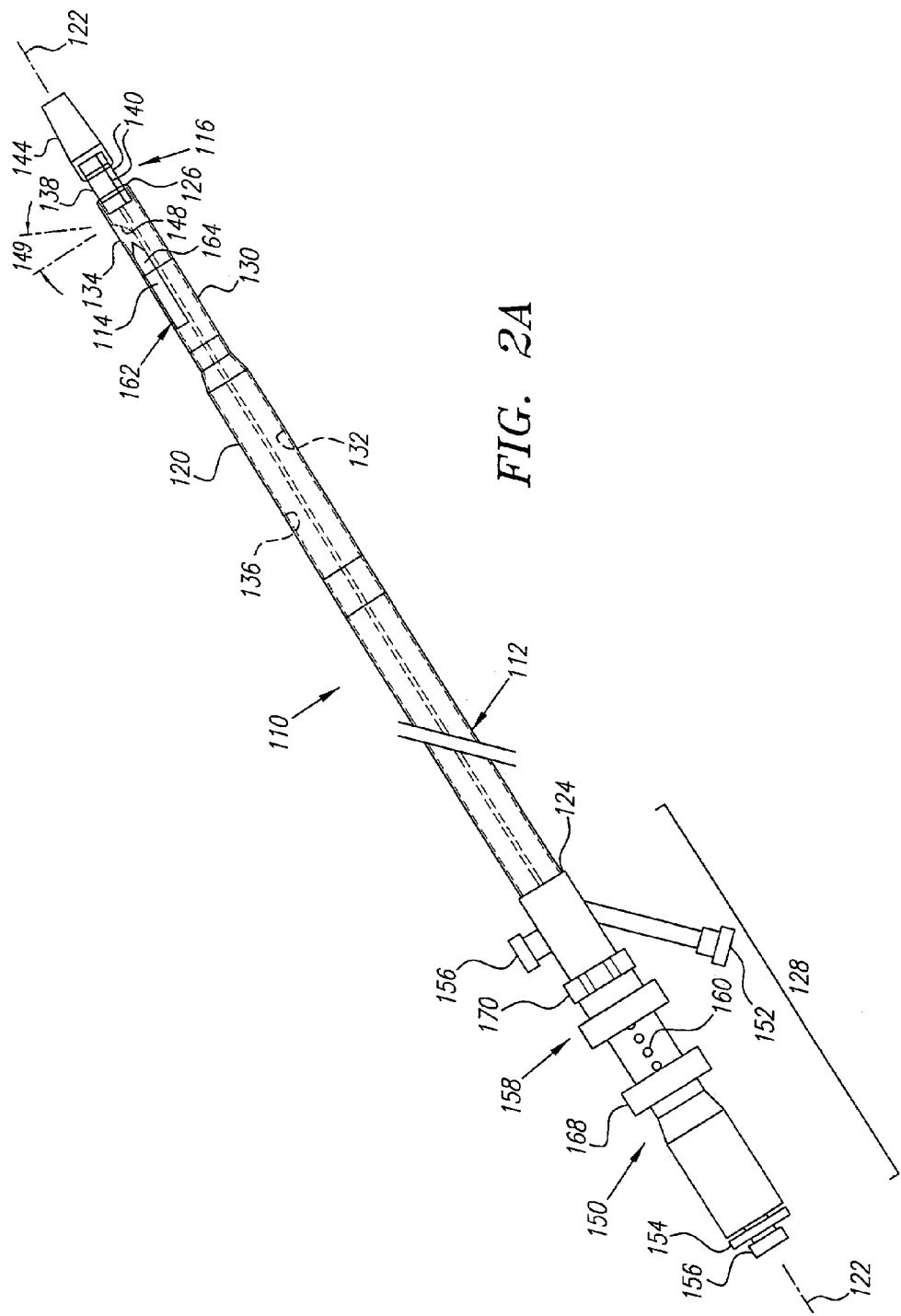
FIG. 2A is a side view of a catheter and needle device for directing a guidewire.
Figure 2B:
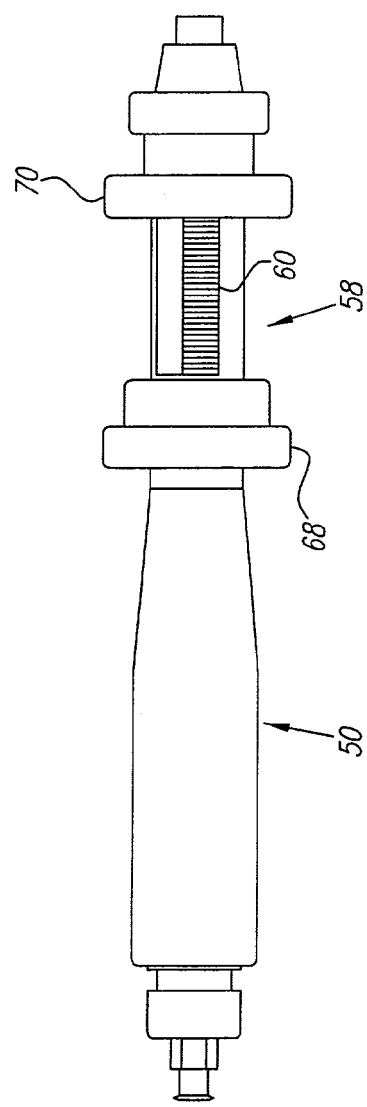
FIGS. 2B and 2C are side views of a handle for the catheter device of FIG. 2A.
Figure 2C:
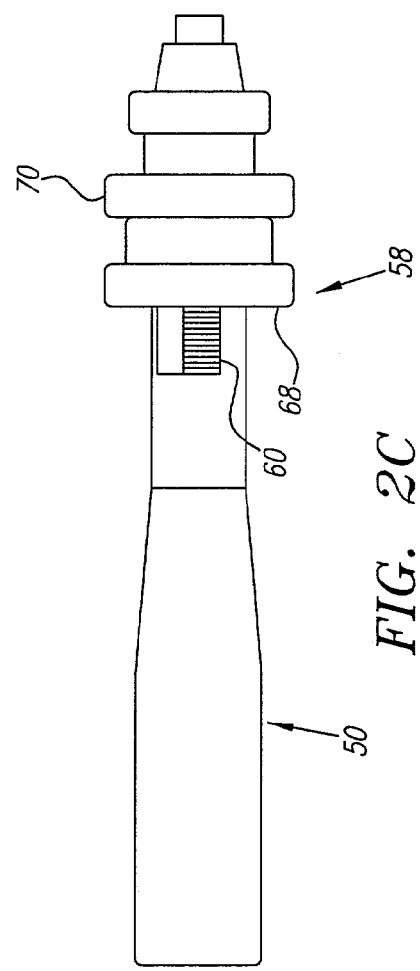
Figure 2D:
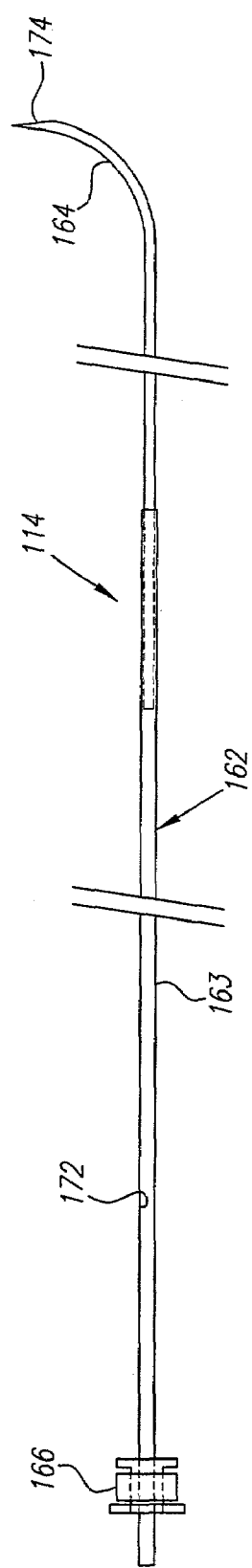
FIG. 2D is a side view of a needle assembly for the catheter device of FIG. 2A.
Figure 2E:
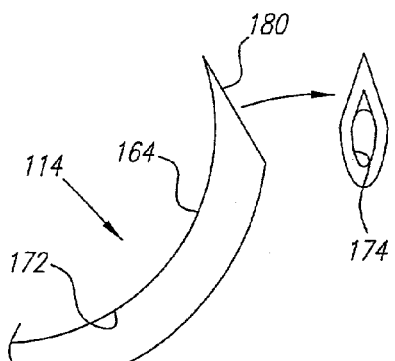
FIGS. 2E and 2F are details of a tip of the needle assembly of FIG. 2D, showing a standard and a reverse bevel, respectively, for directing a guidewire deployed from the tip.
Figure 2F:
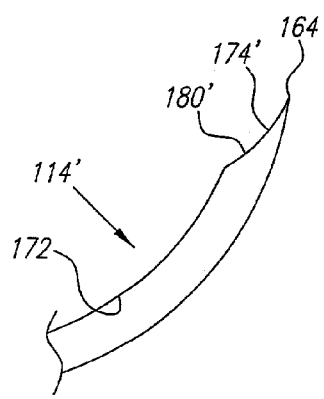
Figure 2G:
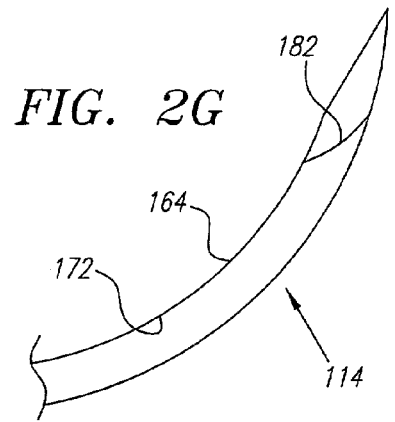
FIGS. 2G and 2H are details of an alternative tip of the needle assembly of FIG. 2D, showing an internal ramp within the tip for directing a guidewire deployed from the tip.
Figure 2H:
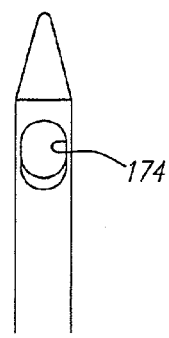

In further alternatives, a catheter device with a needle, such as that shown in FIG. 2A, may be used to place the first guidewire 910 between the first and second vessels 80, 82 directly through the tissue 81 prior to creation of the interstitial channel 84. Channel-creating devices and methods, such as those disclosed in U.S. Ser. No. 08/730,496, filed Oct. 11, 1996, and Ser. No. 09/056,589, filed Apr. 7, 1998, the disclosures of which are expressly incorporated herein by reference, may be used subsequently to create the channel 84. Devices and methods, such as those previously described herein, may then be used to floss the first guidewire 910 between the first and second entry sites.

Figure 12A:
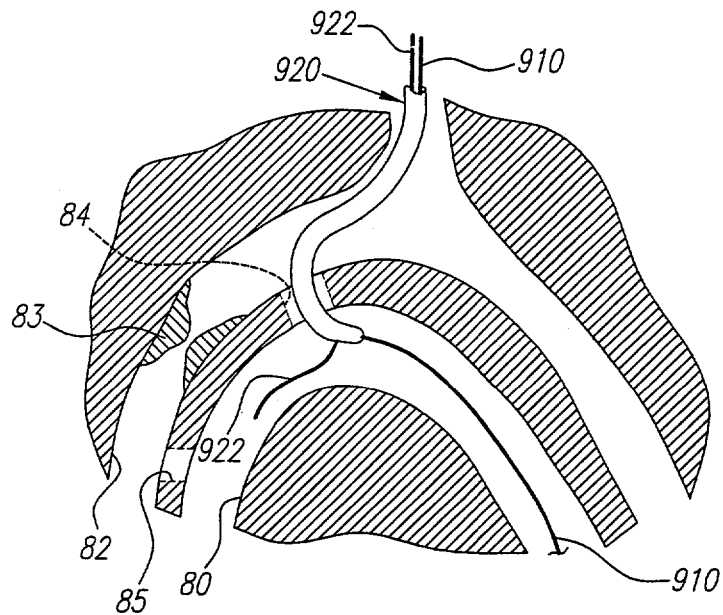
FIGS. 12A-12D are cross-sectional views of a method for placing a guidewire between two adjacent vessels to bypass a stenotic region of one of the vessels.

The flossed first guidewire 910 may then be used in a procedure that involves advancing one or more catheters or other interventional devices over the first guidewire 910 from one or both of the first and second entry sites. For example, as shown in FIGS. 12A-12D, a first guidewire 910, flossed through a first or proximal interstitial channel 84, may be used in a method for bypassing a stenotic or occluded region of a vessel, such as the stenotic region 83 of coronary artery 82. A guidewire directing catheter 920, such as that shown in FIG. 1A or 7A, may be introduced into the second entry site and advanced over the first guidewire 910 through the second vessel 82 and into the first vessel 80. The guidewire directing catheter 920 may be oriented with respect to an upstream portion 80*b* of the first vessel 80, and a third guidewire 922 (an "artery-to-vein" or "a-to-v" wire) may be advanced through the guidewire directing catheter 920 into the upstream portion 80*b* of the first vessel 80 (FIG. 12A). The guidewire directing catheter 920 may then be withdrawn through the second vessel 82 and out of the body through the second entry site.

Figure 12B:
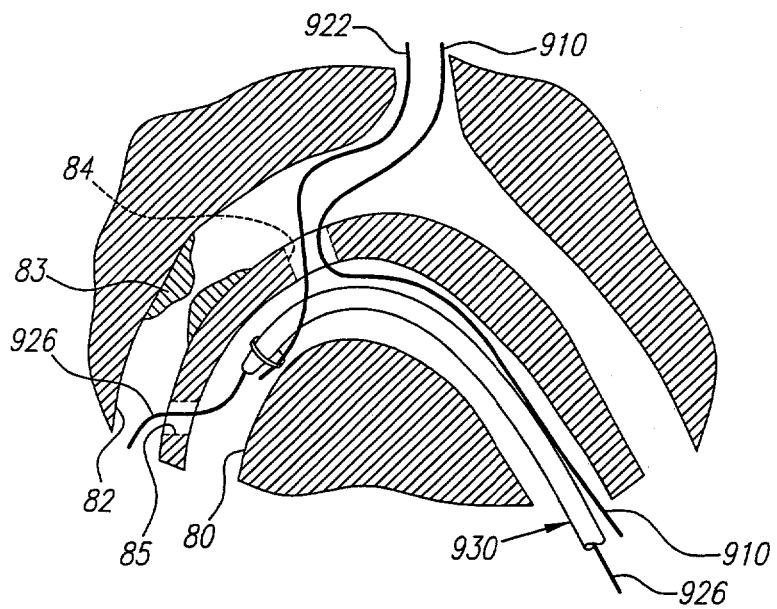

A fourth guidewire 926 may be placed from the first entry site into the first vessel 80 and advanced through a second or distal interstitial channel 85 downstream into the second vessel 82, i.e., away from stenotic region 83, for example, using the devices and methods described above for placing the first guidewire 910 through the first channel 84. A snaring member 930 may then be introduced into the first entry site and advanced over the fourth guidewire 926 into the first vessel adjacent the third guidewire 922 (FIG. 12B).

Figure 12C:
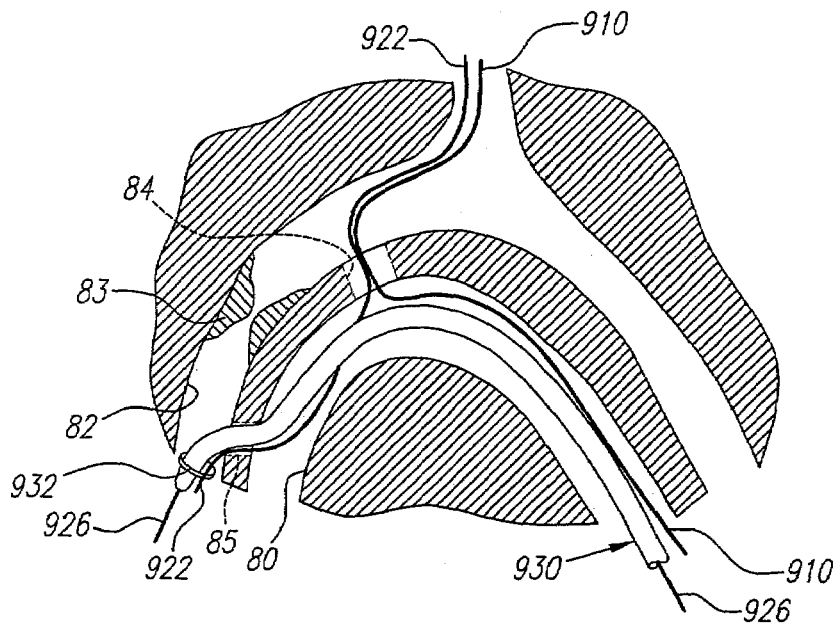

The snare or grasping mechanism 932 on the snaring member 930 may be used to capture the third guidewire 922, similar to the devices and methods described above. The snaring member 930 may then be advanced more distally over the fourth guidewire 926, until the snare 932 and the third guidewire 922 are directed into the second vessel 82 downstream of the stenotic region 83 (FIG. 12C).

Figure 12D:
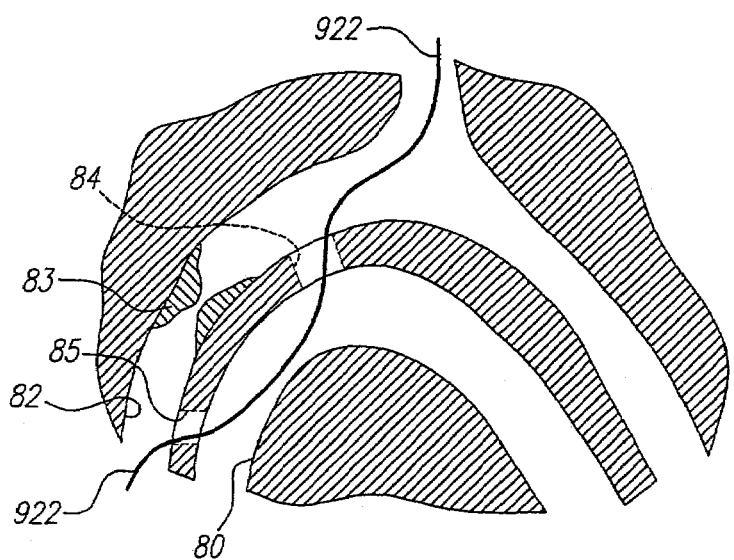

The third guidewire 922 may then be released from the snare 932, and the snaring member 930 withdrawn from the first vessel 80 and out of the body through the first entry site. The fourth guidewire 926 and/or the first guidewire 910 may also be removed from the body or may be left in place to allow advancement of other devices over them. In a preferred form, the guidewire directing and snaring steps may be performed using a single device, such as that shown in FIGS. 7A and 7B, which is capable of directing a guidewire substantially laterally and is capable of deploying a snare or other grasping mechanism. Thus, as shown in FIG. 12D, the third guidewire 922 may be placed from the second entry site, through the second vessel 82, the first channel 84, the first vessel 80, the second channel 85 and finally back into the second vessel 82, thereby bypassing the stenotic region 83.

Subsequent procedures may then be performed, at least partially over the third guidewire 922, such as procedures to further dilate the channel between the vessels, or to deliver a stent graft or other connector to hold open the channel. Co-pending U.S. application Ser. No. 08/970,694, filed Nov. 14, 1997, discloses exemplary procedures which may be performed over a guidewire placed as described previously herein. The disclosure of this reference and any others cited therein is expressly incorporated herein by reference.

Alternatively, it may desirable to minimize the number of guidewires and/or devices introduced into the patient's vasculature. For example, FIGS. 13A and 14A-14F show a proximal lumen snaring catheter 1010 that may be used in a method for placing a guidewire 1006 between first and second adjacent vessels 80, 82, for example, to bypass a stenotic region 83. The snaring catheter 1010 includes a catheter body 1012 and a snaring member 1040 deployable substantially laterally from the catheter body 1012. The catheter body 1012 includes a first lumen 1036 extending between its proximal end (not shown) and a peripheral opening 1034 in its distal portion 1030. The catheter body 1012 also includes a second lumen 1032 that extends between a proximal opening 1031 and a distal opening 1033 to facilitate advancement of the snaring catheter 1010 over a guidewire 1002. The catheter 1010 device may also include an orientation element 1016 and/or an imaging element (not shown), similar to the devices previously described.

Preferably, the proximal opening 1031 of the second lumen 1032 is located on a peripheral surface 1019 proximate to the distal portion 1030 and/or the peripheral opening 1034. The second lumen 1032 may then provide a proximal lumen for substantially reducing the distance that the guidewire 1002 must be pulled to withdraw it from the second lumen 1032, i.e., without having to pull the guidewire 1002 the entire length of the catheter body 1012.

Figure 13B:
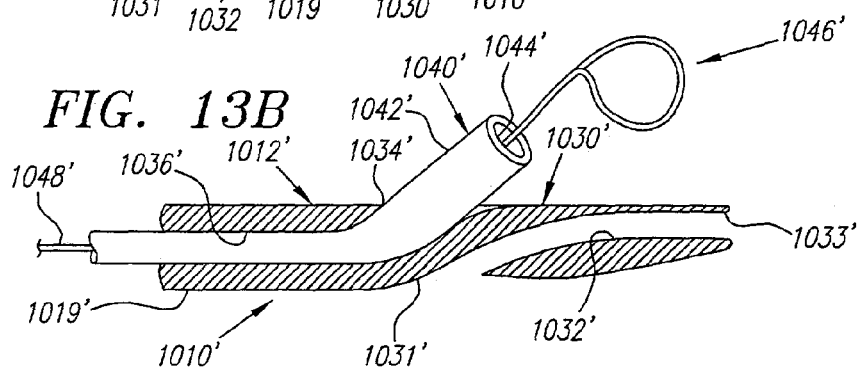

Alternatively, as shown in FIG. 13B, the proximal opening 1031' may be located relatively close to the distal opening 1033', e.g., on the peripheral surface 1019' between the peripheral opening 1034' of the first lumen 1036' and the distal opening 1033' of the second lumen 1032'. This configuration may allow the distal portion 1030' to have a smaller diameter since the second lumen 1032' terminates before the first lumen 1036' begins along the distal portion 1030'. In addition, since the second lumen 1032' generally receives a guidewire or other relatively small diameter rail therethrough, the distal portion 1030' may be further tapered towards the distal opening 1033', without substantially affecting the size of the second lumen 1032'.

The snaring member 1040 includes an elongate sleeve 1042 including a snare lumen 1044 from which a snare 1046 connected to a control wire 1048 may be advanced. The snaring member 1040 may include additional lumens (not shown), e.g., a guidewire lumen to allow the snaring member 1040 to be advanced over a guidewire, and/or may include alternative snare configurations, such as those described previously.

With particular reference to FIGS. 14A-14F, the snaring catheter 1010 may be advanced over first and second guidewires 1004, 1002 placed in the first vessel 80 to direct a third guidewire 1006 between the first and second vessels 80, 82. The first and second guidewires 1004, 1002 are placed between the first and second vessels 80, 82 (FIG. 14A) and a percutaneous entry site (not shown), for example, using a guidewire delivery device, such as the catheter device 110 shown in FIG. 2A. The first and second guidewires 1004, 1002 may be placed directly through tissue 81 or through channels (not shown) extending between the first and second vessels 80, 82.

Figure 14A:
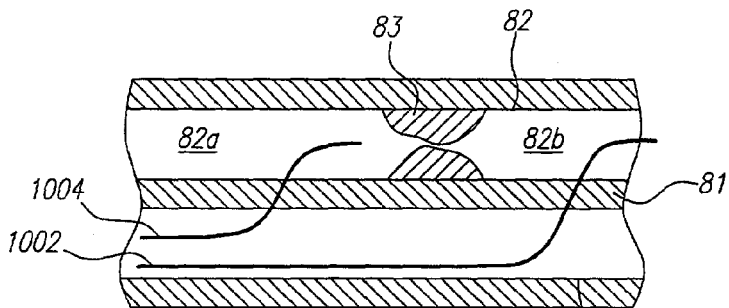
FIGS. 14A-14F are cross-sectional views showing another method for placing a guidewire between two adjacent vessels to bypass a stenotic region of one of the vessels.
Figure 14B:
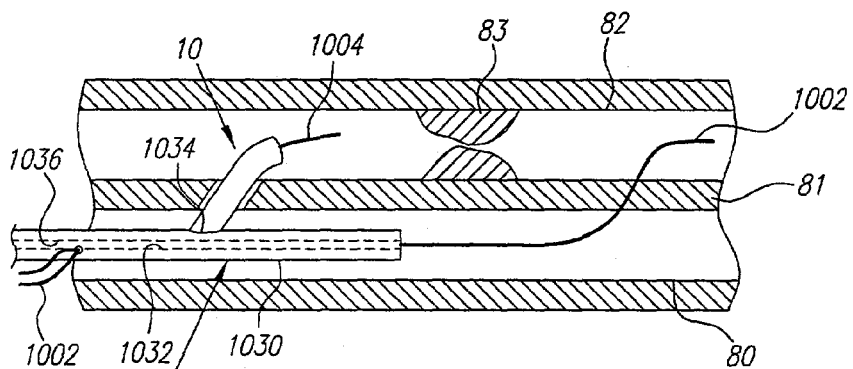

Outside of the body, the first guidewire 1004 is fed proximally through the peripheral opening 1034 into the first lumen 1036 of the snaring catheter 1010, and the second guidewire 1002 is fed proximally through the distal opening 1033 into the second lumen 1032. The distal portion 1030 of the snaring catheter 1010 may then be percutaneously introduced through the entry site and advanced into the first vessel 80. The snaring member 1014 may then be deployed from the peripheral opening 1034 over the first guidewire 1004 and into the second vessel 82 (FIG. 14B). The elongate sleeve 1042 of the snaring member 1040 may include a tapered distal tip (not shown) to further dilate the channel (not shown) between the first and second vessels 80, 82, for example, if the first guidewire 1004 is placed directly through the tissue 81, and/or to facilitate advancement through the channel without snagging on strands of tissue therein (not shown).

The first guidewire 1004 may be withdrawn through the snaring member 1040, e.g., if the snaring member 1040 includes a single lumen for either a guidewire or a snare 1046, or may be left in place, e.g., if the snaring member 1040 includes separate snare and guidewire lumens. Alternatively, the snaring member 1040 may have a puncturing tip (not shown), similar to the needle assembly 114 shown in FIG. 2D, for penetrating the tissue 81. The snaring catheter 1010 may then be directed into the first vessel 80 over the second guidewire 1002, eliminating completely any need for the first guidewire 1004. Once in the first vessel 80, the distal portion 1030 of the snaring catheter 1010 may be oriented with respect to the second vessel 82, and the snaring member 1040 may be advanced directly through the tissue 81 into the second vessel 82.

Figure 14C:
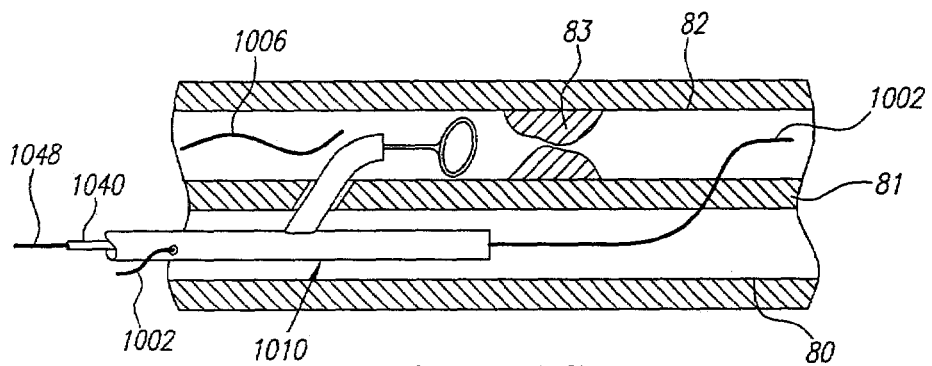

The third guidewire 1006 may be advanced into the second vessel 82, for example, upstream of the stenotic region 83, and the snare 1046 may be advanced from the snare lumen 1044 into the second vessel 82 (FIG. 14C). If necessary, the snare 1046 and/or the third guidewire 1006 may be further manipulated until the third guidewire 1006 is captured in the snare 1046. The snare 1046 may be withdrawn into the snare lumen 1044 to secure the third guidewire 1006 therein, or otherwise to detachably secure the third guidewire 1006 to the snaring member 1040.

Figure 14D:
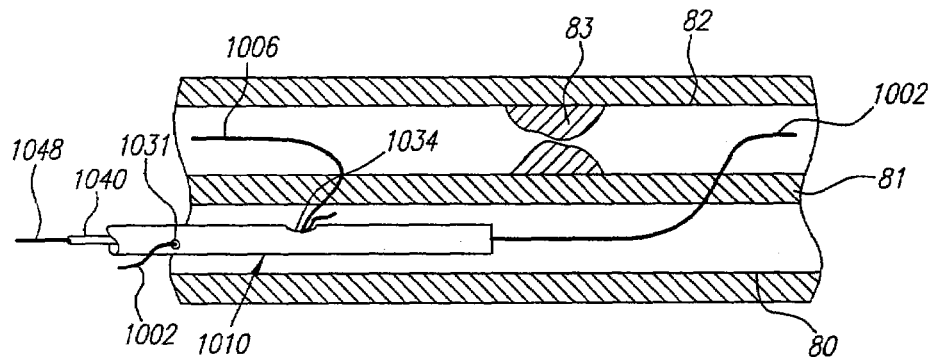
Figure 14E:
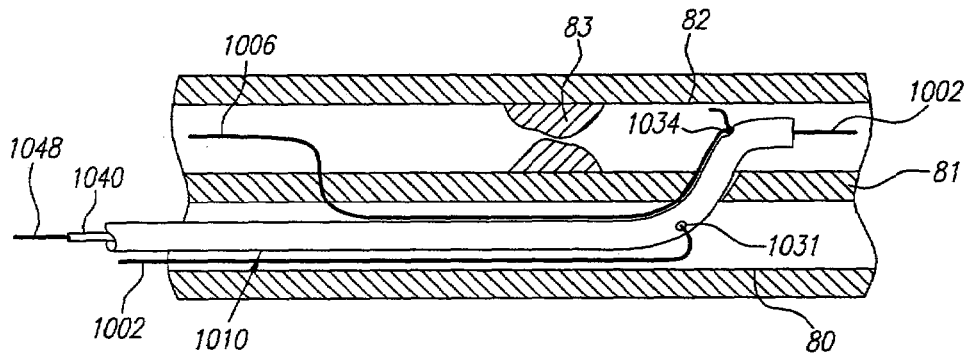
Figure 14F:
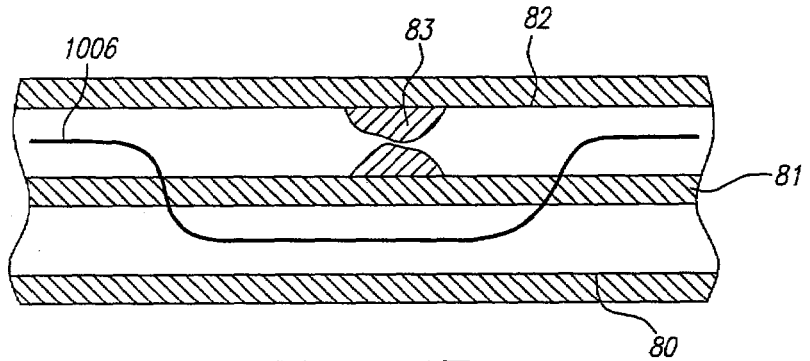

The snaring member 104 may then be withdrawn from the second vessel 82, for example, into the first lumen 1036 of the snaring catheter 1010, to thereby direct the third guidewire 1006 into the first vessel 80 (FIG. 14D). The snaring catheter 1010 may then be advanced over the second guidewire 1002 until the distal portion 1030 enters the second vessel 82, thereby pulling the third guidewire 1006 into the second vessel 82 downstream of the stenotic region 83 (FIG. 14E). The snaring member 1040 and/or the snare 1046 may be deployed, or the third guidewire 1006 may otherwise be released from the snare 1046. The snaring catheter 1010 may then be withdrawn from the second vessel 82 back into the first vessel 80, and out of the body, thereby leaving the third guidewire 1006 in place bypassing the stenotic region 83 of the second vessel 82 via the first vessel 80 (FIG. 14F).

Figure 20A:
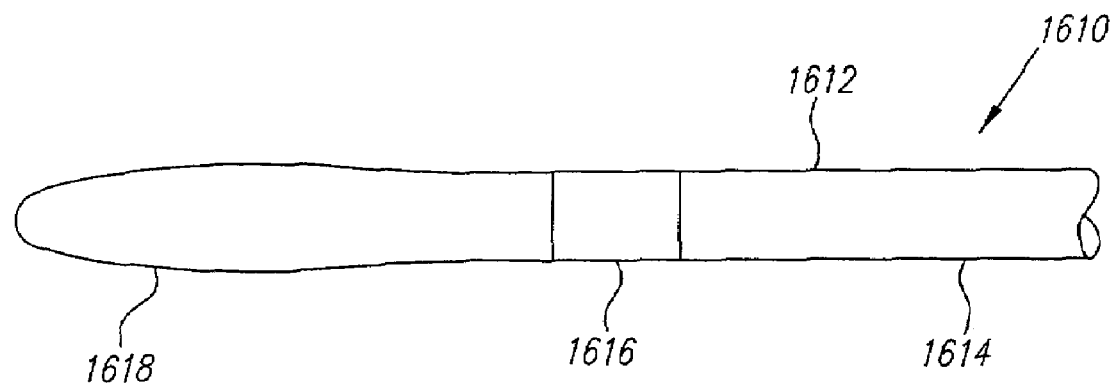
FIG. 20A shows a distal portion of a "self-knuckling" catheter, in accordance with another aspect of the present invention.
Figure 20B:
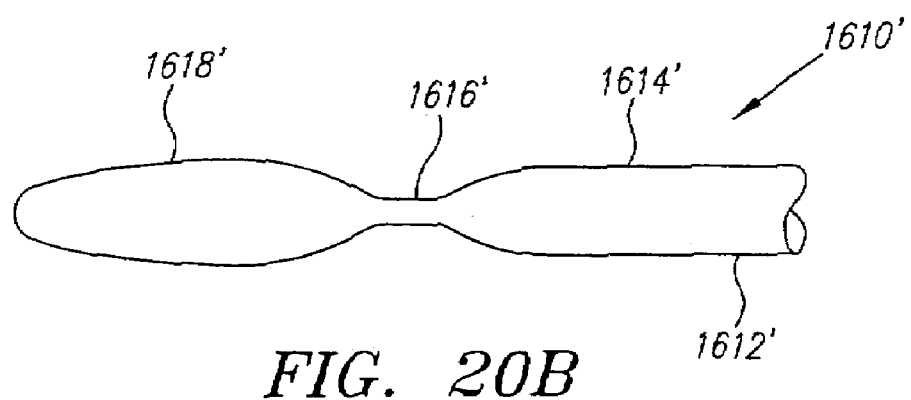
FIG. 20B shows a distal portion of an alternative embodiment of the self-knuckling catheter of FIG. 20A.
Figure 20C:
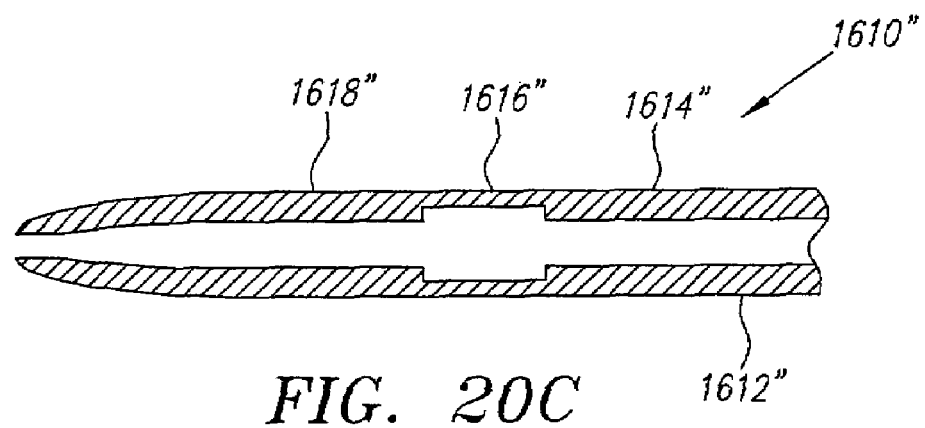
FIG. 20C is a cross-sectional view of another alternative embodiment of the self-knuckling catheter of FIG. 20A.

Turning to FIG. 20A, a distal portion 1612 of a "self-knuckling" catheter 1610 is shown in accordance with another aspect of the present invention. The distal portion 1612 includes a first region 1614, a weakened region 1616, and a second or tip region 1618. The weakened region 1616 may be formed from a material having a Durometer that is substantially less than the materials of the first and second regions 1614, 1618, which may have similar or different Durometers as compared to one another. In an alternative embodiment, shown in FIG. 20B, the weakened region 1616' may be formed from a similar material as the first and second regions 1614', 1618', but may have a substantially reduced cross-section. In another alternative, shown in FIG. 20C, the distal portion 1612" of the catheter 1610" may have a substantially uniform exterior cross-section, but may have a substantially reduced wall thickness at the weakened region 1616". Any one or more combinations of these alternatives may be utilized to provide a weakened region on the distal portion of a catheter that may prolapse when subjected to a substantially lateral force.

Thus, a self-knuckling catheter 1610 in accordance with the present invention may be formed or molded from a single body, having a reduced wall thickness or cross-section at a weakened region 1616 on the distal portion 1612 of the catheter, or may be formed from multiple segments having two or more different Durometers attached together in a predetermined fashion to provide a weakened region 1616. The catheter 1610 preferably has a snare lumen (not shown) from which a snaring element, such as those described above, may be deployed and/or a guidewire lumen (not shown) to facilitate advancement of the catheter 1610 over a guidewire.

Figure 21A:
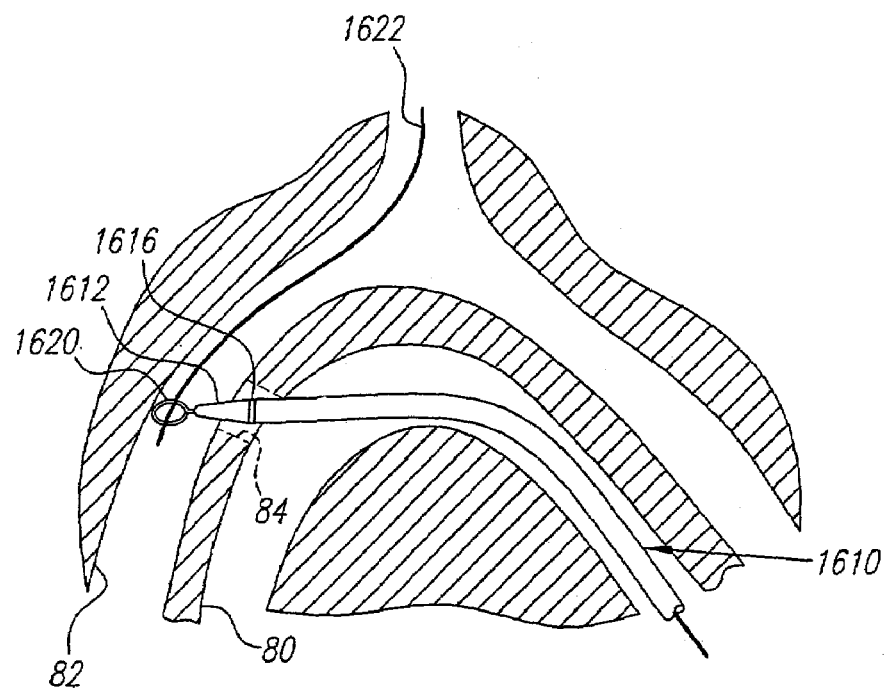
FIGS. 21A-21D are cross-sectional views showing a method of snaring and directing a guidewire using the self-knuckling catheters of FIGS. 20A-20C.

Turning to FIGS. 21A-21D, a method of snaring and/or directing a guidewire using a self-knuckling catheter 1610 is shown. As indicated in FIG. 21A, a guidewire 1622 may be initially advanced into an artery 82 and placed proximate an interstitial channel 84 in communication with an adjacent vein 80. A self-knuckling catheter 1610, such as those described above, may be advanced into the vein 80, for example, over a guidewire (not shown), and through the interstitial channel 84 into the artery 82. A snaring element 1620 may be deployed from the catheter 1610 and manipulated to capture the target guidewire 1622.

Figure 21B:
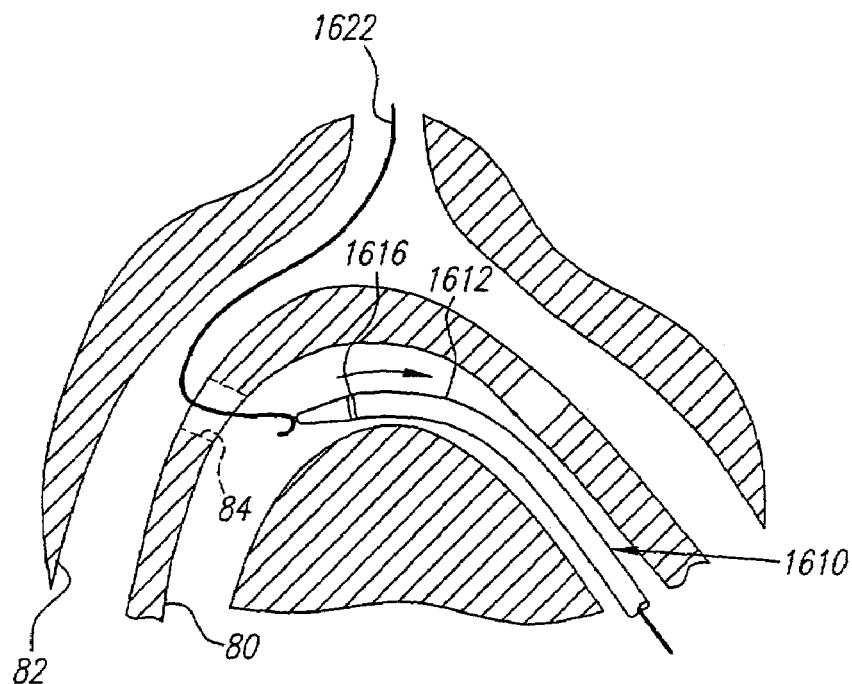
Figure 21C:
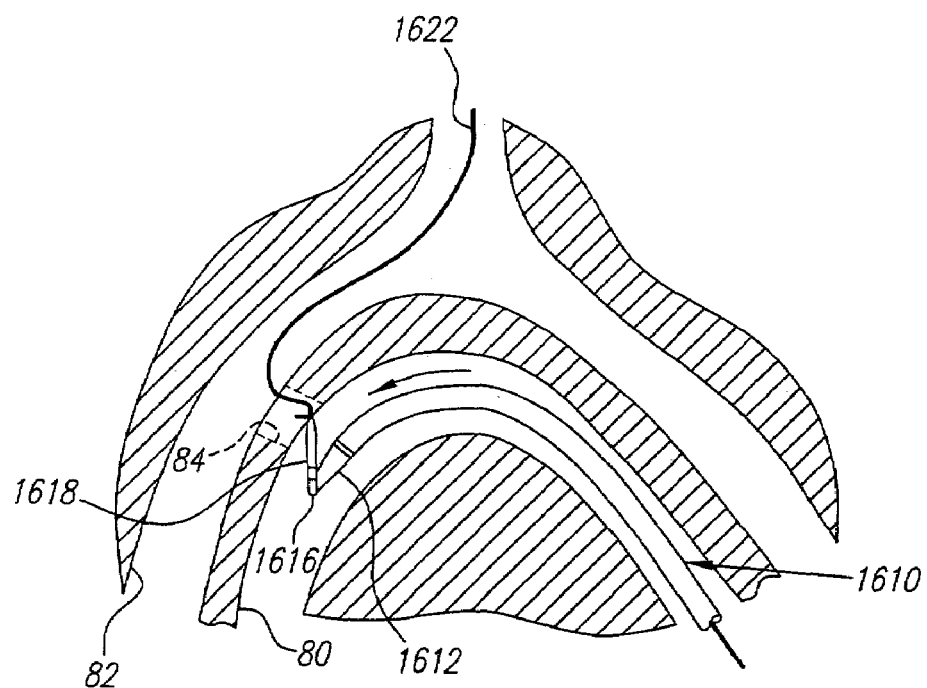

As shown in FIG. 21B, the catheter 1610 may then be withdrawn back into the vein 80, thereby pulling the guidewire 1622 into the vein 80. The catheter 1610 may then be advanced distally within the vein 80 to a selected location, for example, proximate to or into a second interstitial channel (not shown), similar to the methods previously described. As described above, the distal portion 1612 of the catheter 1610 preferably includes a weakened region 1616. As the distal portion 1612 is advanced distally beyond the interstitial passage 84, the distal portion 1612 will "knuckle," i.e., bend or fold over, at the weakened region 1616, as shown in FIG. 21C.

Figure 21D:
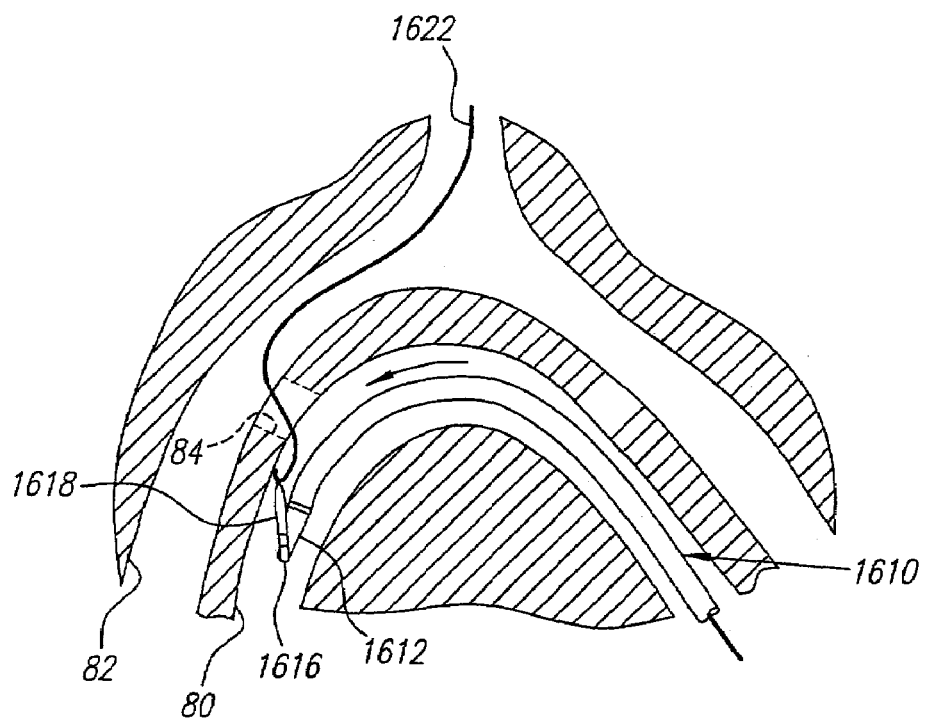

Because of the tension on the guidewire 1622, a substantially lateral force may be applied to the distal portion 1612, pulling the tip region 1618 towards the interstitial channel 84 as the distal portion 1612 is advanced distally past the interstitial channel 84. Because of the higher relative stiffness of the distal portion 1612 adjacent the weakened region 1616, a prolapse may be created in the catheter 1610 at the weakened region 1616, resulting in a knuckled distal portion. The knuckled distal portion 1612 may provide a substantially atraumatic tip that facilitates the advancement of the catheter 1610 distally into the vein 80 without substantial risk of the tip 1618 of the catheter 1610 entering a small side branch (not shown) of the vein 80 and/or damaging the wall of the vein 80. The distal portion 1612 may be advanced distally beyond the interstitial channel 84, as shown in FIG. 21D, to a selected location, where the guidewire 1622 may be released and/or otherwise manipulated, similar to the methods previously described herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A catheter for directing a guidewire substantially laterally with respect to a body passage within which the catheter is introduced, comprising:
   an elongate member having proximal and distal ends, having a distal portion adapted for insertion within a body passage, and defining a longitudinal axis and an outer peripheral surface; a first lumen extending proximally from a first axial opening in the distal end; and a second lumen extending between the proximal end of the elongate member and a second lumen lateral opening in the distal portion proximate the distal end;
   wherein the distal portion comprises an angled step tapering to a distal tip, the second lumen lateral opening being located on the angled step; and
   a snaring member deployable from the second lumen lateral opening, said snaring member comprising a loop extending distally from the second lumen lateral opening and surrounding the distal portion of the elongate member such that as the snaring member is directed proximally and distally, the loop substantially engages and disengages, respectively, the outer surface of the elongate member.

2. The catheter of claim 1, wherein the second lumen lateral opening is located on the peripheral surface of the elongate member.

3. The catheter of claim 1, wherein the second lumen includes a deflection ramp adjacent the second lumen lateral opening.

4. The catheter of claim 1, wherein the first lumen has a peripheral opening proximate the first axial opening.

5. A system comprising a catheter according to claim 1, further in combination with a snaring member that is deployable from the second lumen lateral opening.

6. The system of claim 5, wherein the snaring member comprises a loop that is advanceable out of the second lumen lateral opening so as to surround the distal portion of the elongate member such that, as the snaring member is directed proximally and distally, the loop substantially engages and disengages, respectively, the outer surface of the elongate member.

7. A catheter for directing a device substantially laterally with respect to a body passage within which the catheter is introduced, comprising:
   an elongate member having proximal and distal ends, having a distal portion adapted for insertion within a body passage, and defining a longitudinal axis and an outer peripheral surface;
   first lumen extending between the proximal end of the elongate member and a lateral opening in the distal portion proximate the distal end; and
   a snaring member comprising a loop extending distally from the lateral opening and surrounding the distal portion of the elongate member such that as the snaring member is directed proximally and distally, the loop substantially engages and disengages, respectively, the outer surface of the elongate member.

8. The catheter of claim 7, wherein the lateral opening is located on the peripheral surface of the elongate member.

9. The catheter of claim 7, wherein the lumen includes a deflection ramp adjacent the lateral opening.

10. The catheter of claim 7, wherein the distal portion comprises an angled step tapering to a distal tip, the lateral opening being located on the angled step.

11. The catheter of claim 7, further comprising a second lumen extending proximally from an axial opening in the distal end.

12. The catheter of claim 11, wherein the second lumen has a peripheral opening proximate the first axial opening.

13. The catheter of claim 11, wherein the snaring member comprises a looped wire having first and second ends extending proximally through the first and second lumens, respectively, to define the loop.

14. The catheter of claim 7, wherein the device comprises a guidewire, the snaring member configured for capturing the guidewire when the loop engages the outer surface of the elongate member.

15. The catheter of claim 7, wherein the loop is biased to assume an enlarged substantially circular configuration.

16. The catheter of claim 15, wherein the substantially circular configuration defines a predetermined diameter corresponding to a diameter of a lumen of a blood vessel, and wherein the distal portion of the elongate member has a diameter substantially smaller than the predetermined diameter.

17. The catheter of claim 7, wherein the distal portion comprises an angled step tapering to a distal tip, the lateral opening being located on the angled step.

18. A catheter for directing a guidewire substantially laterally with respect to a body passage within which the catheter is introduced, said catheter comprising: an elongate member having proximal and distal ends, having a distal portion adapted for insertion within a body passage, and defining a longitudinal axis and an outer peripheral surface; a first lumen extending proximally from a first axial opening in the distal end; and a second lumen extending between the proximal end of the elongate member and a second lumen lateral opening in the distal portion proximate the distal end; and
   a snaring member deployable from the second lumen lateral opening, said snaring member comprising a loop that is advanceable distally from the second lumen lateral opening so as to surround the distal portion of the elongate member such that, as the snaring member is directed proximally and distally, the loop substantially engages and disengages, respectively, the outer surface of the elongate member.

19. The catheter of claim 18, wherein the second lumen lateral opening is located on the peripheral surface of the elongate member.

20. The catheter of claim 18, wherein the second lumen includes a deflection ramp adjacent the second lumen lateral opening.

21. A catheter system for directing a guidewire substantially laterally with respect to a body passage within which the catheter is introduced, said catheter comprising:

an elongate member having proximal and distal ends, a distal portion adapted for insertion within a body passage, a longitudinal axis, an outer peripheral surface, a first lumen extending proximally from an axial opening in the distal end and a second lumen extending between the proximal end of the elongate member and an unobstructed second lumen lateral opening in the distal portion proximate the distal end;

wherein the first lumen also has a peripheral opening proximate the axial opening;

wherein a deflection ramp is located within the second lumen adjacent the second lumen lateral opening;

a guidewire having a distal end, the guidewire being advanceable through the second lumen such that the distal end of the guidewire will be deflected by the deflection ramp and will then advance out of the second lumen lateral opening; and an orientation element located on a distal portion of the catheter, said orientation element being usable in conjunction with an imaging device to enable the user to adjust the rotational orientation of the catheter within the body such that the guidewire will advance toward an intended target location as the guidewire exits the second lumen lateral opening.

22. The catheter system of claim 21, wherein the second lumen lateral opening is located on the peripheral surface of the elongate member.

* * * * *